US012076481B2

(12) United States Patent
Cottenden et al.

(10) Patent No.: US 12,076,481 B2
(45) Date of Patent: Sep. 3, 2024

(54) MEDICAMENT DELIVERY DEVICE

(71) Applicant: TTP PLC, Royston (GB)

(72) Inventors: David Cottenden, Royston (GB); Jianye Wang, Royston (GB); Duncan Young, Royston (GB); Desmond Cheung, Royston (GB); Simon Waddelow, Royston (GB); Iain McDerment, Royston (GB); Rob Selby, Royston (GB); Catherine Wyman, Royston (GB); Rob May, Royston (GB); Chris Groombridge, Royston (GB)

(73) Assignee: TTP PLC, Royston (GB)

( * ) Notice: Subject to any disclaimer, the term of this patent is extended or adjusted under 35 U.S.C. 154(b) by 809 days.

(21) Appl. No.: 17/273,203

(22) PCT Filed: Sep. 3, 2019

(86) PCT No.: PCT/GB2019/052452
§ 371 (c)(1),
(2) Date: Mar. 3, 2021

(87) PCT Pub. No.: WO2020/049289
PCT Pub. Date: Mar. 12, 2020

(65) Prior Publication Data
US 2021/0322686 A1 Oct. 21, 2021

(30) Foreign Application Priority Data

Sep. 3, 2018 (GB) .................................. 1814300
Apr. 18, 2019 (GB) .................................. 1905545

(51) Int. Cl.
A61M 15/00 (2006.01)

(52) U.S. Cl.
CPC .... *A61M 15/0051* (2014.02); *A61M 15/0055* (2014.02); *A61M 2202/064* (2013.01)

(58) Field of Classification Search
CPC .............. A61M 15/00; A61M 15/0046; A61M 15/005; A61M 15/0051; A61M 15/0053;
(Continued)

(56) References Cited

U.S. PATENT DOCUMENTS 4,090,642 A 5/1978 Baker et al.
5,447,151 A 9/1995 Bruna et al.
(Continued)

FOREIGN PATENT DOCUMENTS

CN 1622838 A 6/2005
EP 2929905 A1 10/2015
(Continued)

OTHER PUBLICATIONS

International Search Report and Written Opinion issued for PCT/GB2019/052450, Dated Dec. 6, 2019, 9 pages.
(Continued)

Primary Examiner — Kendra D Carter
Assistant Examiner — Jaeick Jang

(57) ABSTRACT

A manifold for a medicament delivery device configured to deliver discrete doses of medicament contained in a plurality of individual compartments spaced along a carrier strip and sealed by a sealing layer to form a medicament carrier, the manifold comprising: at least one opening mechanism comprising a release member arranged to engage between the carrier strip and the sealing layer of a medicament carrier so as to separate the sealing layer from the carrier strip and thereby open a compartment of the medicament carrier as it is advanced into an entrainment position; wherein the release member includes a surface configured to cover the opened compartment when in the entrainment position so as
(Continued)

substantially to contain the medicament dose of said opened compartment.

12 Claims, 18 Drawing Sheets

(58) Field of Classification Search
CPC .......... A61M 15/0055; A61M 15/0058; A61M 2202/06; A61M 2202/062; A61M 2202/064; A61M 15/0065; A61M 15/0068; A61M 15/007; A61M 15/0071; A61M 15/0073; A61M 15/008; A61M 15/0003; A61M 15/0006; A61M 15/0021; A61M 15/0023; A61M 15/0025; A61M 15/0043; A61M 15/0045
See application file for complete search history.

(56) References Cited

U.S. PATENT DOCUMENTS

| | | | |
|---|---|---|---|
| 6,792,945 B2 * | 9/2004 | Davies | A61M 15/0078 128/203.15 |
| 7,434,579 B2 | 10/2008 | Young et al. | |
| 7,624,733 B2 | 12/2009 | Riley et al. | |
| 7,779,839 B2 | 8/2010 | Pocock et al. | |
| 7,950,389 B2 | 5/2011 | Eason et al. | |
| 8,225,784 B2 | 7/2012 | Sallak et al. | |
| 8,322,336 B2 | 12/2012 | Pocock et al. | |
| 8,474,453 B2 * | 7/2013 | Eason | A61M 15/0051 128/203.15 |
| 8,561,608 B2 | 10/2013 | Chopard | |
| 8,640,695 B2 | 2/2014 | Colomb et al. | |
| 8,746,243 B2 | 6/2014 | Kirniak | |
| 9,789,269 B2 | 10/2017 | Colomb et al. | |
| 9,872,963 B2 | 1/2018 | Kirniak | |
| 2005/0154491 A1 * | 7/2005 | Anderson | A61M 15/00 700/236 |
| 2007/0114237 A1 | 5/2007 | Pirottavio | |
| 2015/0083129 A1 | 3/2015 | Colomb et al. | |
| 2015/0297841 A1 * | 10/2015 | Ono | A61M 15/0055 128/203.15 |
| 2021/0316091 A1 | 10/2021 | Cottenden et al. | |

FOREIGN PATENT DOCUMENTS

| | | | |
|---|---|---|---|
| WO | 03061743 A1 | 7/2003 | |
| WO | 2003061744 A1 | 7/2003 | |
| WO | 2005014089 A1 | 2/2005 | |
| WO | 2010133323 A1 | 11/2010 | |
| WO | WO2011/129789 | 10/2011 | |
| WO | WO-2012012827 A1 * | 2/2012 | ........ A61M 15/0038 |

OTHER PUBLICATIONS

International Search Report and Written Opinion issued for PCT/GB2019/052452, Dated Dec. 6, 2019, 9 pages.
International Search Report and Written Opinion for PCT/GB2020/050498, mailed May 27, 2020.
Combined Search and Examination Report for GB Application No. 1814300.8, dated Oct. 8, 2018.
Combined Search and Examination Report for GB Application No. 1905545.8, dated Oct. 9, 2019.
Office Action for CN Application No. 201980057324.X, mailed Apr. 13, 2022.
Office Action for U.S. Appl. No. 17/273,187, mailed Dec. 7, 2023.
Final Office Action for U.S. Appl. No. 17/273,187, mailed Mar. 27, 2024.

* cited by examiner

MEDICAMENT DELIVERY DEVICE

CROSS-REFERENCE TO RELATED APPLICATIONS

This application is a U.S. national stage filing under 35 U.S.C. 371 of International Application No. PCT/GB2019/052452, entitled "MEDICAMENT DELIVERY DEVICE," filed Sep. 3, 2019, which claims priority to GB Application No. 1814300.8, entitled "MEDICAMENT DELIVERY DEVICE," filed Sep. 3, 2018, and GB Application No. 1905545.8, entitled "MEDICAMENT DELIVERY DEVICE," filed Apr. 18, 2019.

BACKGROUND TO THE INVENTION

The present invention relates to medicament delivery devices, and more specifically to devices and methods for the delivery of aerosolised "dry powder" medicament.

It is well-known to store individual medicament doses (e.g. in the form of a dry powder) in a medicament carrier that comprises a plurality of compartments spaced apart regularly along an elongate carrier strip, wherein the majority of the compartments (e.g. depressions in the surface of the medicament carrier) are each filled with a measured dose of medicament. The compartments are typically "lozenge" shaped with each compartment being orientated in a transverse direction across the carrier strip. A removable sealing layer (e.g. a laminated backing) is secured (e.g. welded) over the carrier strip to provide a moisture barrier seal that contains the medicament doses within the individual compartments. The sealing layer can then be gradually removed (e.g. peeled back) to expose the individual medicament doses, one at a time, as required. Such a medicament carrier may be known as a "blister strip", with the individual compartments being referred to as "blisters".

While various devices are known for delivering medicament from a single medicament carrier, an increasing number of inhaled drug therapies involve combinations of two dry powder formulations, which are not chemically stable when mixed. This leaves the option of delivering those formulations using two different inhalers, or using a medicament delivery device which can store the formulations separately until the medicament is required, at which time the separate formulations are combined immediately prior to or during inhalation so that a user inhales both dry powder formulations in one breath.

The latter option of a single device is much more attractive, since it is far easier for the user to take the medicine, and would therefore be expected to increase the probability of adherence to the prescribed dosing regimen by a user. In such a device, two medicament carriers may each store different medicament doses, which are intended to be mixed together immediately prior to or during inhalation.

One such device, which can store such formulations on separate medicament carriers (such as those described above) until inhalation of the medicament is required, is described in WO 2003/061743 and WO 2005/014089, for example.

A peeling mechanism is arranged to cause a portion of the sealing layer on the carrier strip to be peeled away, on each of the two carrier strips, respectively, when the device is primed. As the sealing layer is removed, the medicament dose that was contained in the compartment, by the sealing layer, is exposed to an aerosolisation chamber that forms part of a manifold of the device. Thus, when a user inhales through the device the exposed medicament (e.g. powder formulation) is aerosolised. Said peeling mechanism is essentially a wedge shaped projection that is arranged to separate the sealing layer from the carrier strip of the medicament carrier.

The peeling mechanism is arranged such that the separated portions of sealing layer and (opened) carrier strip are thereby required to be separately handled, spooled and tensioned, in addition to handling, spooling and tensioning the incoming medicament carrier (i.e. the sealed carrier strip), all within the device. In particular, the incoming carrier strip and the outgoing sealing layer need to have location and tension (respectively) tightly controlled. Since there are two medicament carriers, a total of six components (i.e. the incoming carrier strips with the sealing layers attached, the outgoing carrier strips and the outgoing (separated) sealing layers of each medicament carrier) have to be controlled, co-ordinated, and—for two of them—tensioned.

This known device therefore requires numerous mechanical parts to handle the two medicament carriers and their separated components. Requiring two of every component inside the medicament delivery device results in a device composed of many parts. As a result, this device is presumed to be both complicated and expensive to produce. In particular, installing the medicament carriers at the correct tension would seem to be complicated. Furthermore, the exposed medicament doses are vulnerable to being spilled from the opened compartments if the device is knocked or tilted after being primed, which can result in an inhaled dose containing a lower dosage of formulation than required and spilled formulation being retained within the device, for example.

The present invention aims to provide an improved device and method for delivering medicament from such medicament carriers.

STATEMENT OF INVENTION

Disclosed herein is a manifold for a medicament delivery device configured to deliver discrete doses of medicament contained in a plurality of individual compartments spaced along a carrier strip and sealed by a sealing layer to form a medicament carrier, the manifold comprising: at least one opening mechanism comprising a release member arranged to engage between the carrier strip and the sealing layer of a medicament carrier so as to separate the sealing layer from the carrier strip and thereby open a compartment of the medicament carrier as it is advanced into an entrainment position; wherein the release member includes a surface configured to cover the opened compartment when in the entrainment position so as substantially to contain the medicament dose of said opened compartment.

Preferably, the release member is further configured to provide an inlet and an outlet for air to pass through the opened compartment, when covered by the release member in the entrainment position, such that air can be directed through the opened compartment, via said surface of the release member, to entrain the medicament dose of said opened compartment, said release member thereby forming part of an entrainment airpath.

Preferably, the opening mechanism further comprises a cylindrical indexing wheel having a plurality of indentations spaced around its exterior surface, each indentation configured to receive a compartment of the medicament carrier therein such that rotation of the indexing wheel advances the medicament carrier and thereby moves compartments of the medicament carrier sequentially into the entrainment position.

Preferably, the indexing wheel is positioned adjacent said surface of the release member such that the separated carrier strip passes between the indexing wheel and the release member.

Preferably, while in the entrainment position, the opened compartment is retained within the indentation of the indexing wheel into which it is received, whereby subsequent rotation of the indexing wheel allows the compartment to be released from said indent.

Preferably, the indexing wheel (and/or, optionally, a bearing shaft upon which it is mounted) has an axial through-bore arranged to be in fluid communication with a side of said surface of the release member arranged to face the carrier strip such that the indexing wheel and the release member thereby form part of an entrainment airpath.

Preferably, the entrainment airpath is arranged to flow through the indexing wheel and then along said surface of the release member such that air flows in a first direction through the indexing wheel and then in a second direction along said surface of the release member, said first and second directions being generally opposed.

Preferably, said entrainment airpath is arranged to flow through the indexing wheel from a proximal end of the indexing wheel to a distal end of the indexing wheel, and then return along said surface of the release member from a distal end of the release member to a proximal end of the release member.

Preferably, said surface of the release member comprises at least one structural feature located on a side of said surface arranged to face the carrier strip, said structural feature being configured to disrupt the flow of air across said surface of the release member so to promote air flow through the opened compartment.

Preferably, the at least one feature is configured to disrupt any vorticity in the airflow.

Preferably, the release member comprises at least one curved surface arranged to bridge across a compartment when in the entrainment position.

Preferably, the release member has a leading edge configured to engage between the carrier strip and sealing layer, and a recess is formed in a portion of the leading edge of the release member.

Preferably, the recessed portion extends across a central portion of the leading edge.

Preferably, a bypass airpath is arranged to direct air to bypass the release member of the opening mechanism, wherein the entrainment airpath and the bypass airpath are arranged to merge downstream of the release member of the opening mechanism.

Preferably, the bridging member is configured to isolate at least part of the bypass airpath from the entrainment airpath such that air flowing along the entrainment airpath can only merge with air flowing along the bypass airpath once it has passed across the surface of said release member.

Preferably, a bridging portion defines part of the bypass airpath, the bridging portion comprising at least one aperture via which air can flow into the entrainment airpath and at least one aperture via which bypass air can bypass the entrainment airpath.

Preferably, the entrainment airpath passes beneath the bridging member before passing through the release member.

Preferably, said at least one opening mechanism comprises a first opening mechanism and a second opening mechanism, each opening mechanism being arranged to handle a separate medicament carrier.

Preferably, the first opening mechanism forms part of a first entrainment airpath and the second opening mechanism forms part of a second entrainment airpath, wherein said first and second entrainment airpaths are kept separate such that no mixing between the airpaths occurs.

Also disclosed herein is medicament delivery device, comprising a manifold according to any of the above clauses and/or comprising any of the features described herein either individually or in any suitable combination.

Preferably, a tensioning mechanism is configured to alter a path length along which the separated sealing layer travels through the medicament delivery device so as to regulate tension in at least a portion of the separated sealing layer.

Preferably, said portion of sealing layer extends between the opening mechanism and the tensioning mechanism.

Preferably, the tensioning mechanism comprises one or more resiliently deformable biasing member.

Preferably, the tensioning mechanism is operable to regulate said tension in said portion of the separated sealing layer so as to promote advancement of the separated sealing layer relative to the opening mechanism.

Preferably, the tensioning mechanism (further) comprises a pair of gearwheels having interlocking teeth arranged to engage the separated sealing layer therebetween such that rotation of the gearwheels causes deformation of the separated sealing layer between the interlocking teeth which deformation alters the tension in said portion of separated sealing layer.

Preferably, each of the pair of gearwheels is independently sprung so as to allow a distance between the axis (or axes) of rotation of each of said pair of gearwheels to change.

Preferably, at least one spool is arranged to retain together thereon separated portions of carrier strip and sealing layer of the medicament carrier.

Also disclosed herein is a medicament delivery device for dispensing discrete doses of medicament contained in a plurality of individual compartments spaced along a carrier strip and sealed by a sealing layer to form a medicament carrier, the device comprising: at least one opening mechanism configured to open a compartment of the medicament carrier by separating the sealing layer from the carrier strip as the medicament carrier is advanced though the device; and a tensioning mechanism configured to alter a path length along which the separated sealing layer travels through the medicament delivery device so as to regulate tension in at least a portion of the separated sealing layer.

Preferably, said portion of sealing layer extends between the opening mechanism and the tensioning mechanism.

Preferably, the tensioning mechanism comprises one or more resiliently deformable biasing member.

Preferably, the tensioning mechanism is operable to regulate said tension in said portion of the separated sealing layer so as to promote advancement of the separated sealing layer relative to the opening mechanism.

Preferably, the tensioning mechanism (further) comprises a pair of gearwheels having interlocking teeth arranged to engage the separated sealing layer therebetween such that rotation of the gearwheels causes deformation of the separated sealing layer between the interlocking teeth which deformation alters the tension in said portion of separated sealing layer.

Preferably, each of the pair of gearwheels is independently sprung so as to allow a distance between the axis (or axes) of rotation of each of said pair of gearwheels to change.

Preferably, at least one spool is arranged to retain together thereon separated portions of carrier strip and sealing layer of the medicament carrier.

Preferably, the device is a dry powder inhaler device arranged to delivery medicament from at least one medicament carrier containing a plurality of doses of dry powder medicament.

Preferably, said at least one opening mechanism comprises a first opening mechanism and a second opening mechanism, each opening mechanism being arranged to handle a separate medicament carrier, and the separated portions of sealing layer of the two medicament carriers are retained together on a single take-up spool.

Preferably, the separated portions of sealing layer are retained together downstream of the tensioning mechanism.

Preferably, the take-up spool comprises a friction clutch configured to allow limited slip when a predetermined tension is exceeded in at least one of the separated portions of sealing layer.

As used herein, the term "entrain" preferably connotes to de-aggregate the (e.g. dry powder) medicament in the air (i.e. to "aerosolise" the medicament). Furthermore, as used herein, the term "entrained air" preferably connotes air containing aerosolised medicament.

As used herein, the terms "upstream" and "downstream" preferably connote positions in the air flow path relative to the release mechanism, for example wherein upstream of the release mechanism is before to release of the medicament and downstream of the release mechanism is after release of the medicament. Also, as used herein, the terms flowpath and passageway may be interchangeable.

As used herein, means plus function features may be expressed alternatively in terms of their corresponding structure.

Any apparatus feature described herein may be provided as a method feature, and vice versa. Moreover, it will be understood that the present invention is described herein purely by way of example, and modifications of detail can be made within the scope of the invention. Furthermore, it will be understood by the skilled person that particular combinations of the various features described and defined herein may be implemented and/or supplied and/or used independently. In particular, it will be understood by the skilled person that any feature described in relation to a particular aspect herein may also be applied to another aspect described herein, in any appropriate combination.

As will be recognised by a skilled person, numerous advantages over the prior art are provided by the inventive concepts disclosed herein.

BRIEF DESCRIPTION OF THE DRAWINGS

An embodiment of the present invention will now be described, by way of example only, with reference to the accompanying figures, in which.

DETAILED DESCRIPTION

Figure 1B:
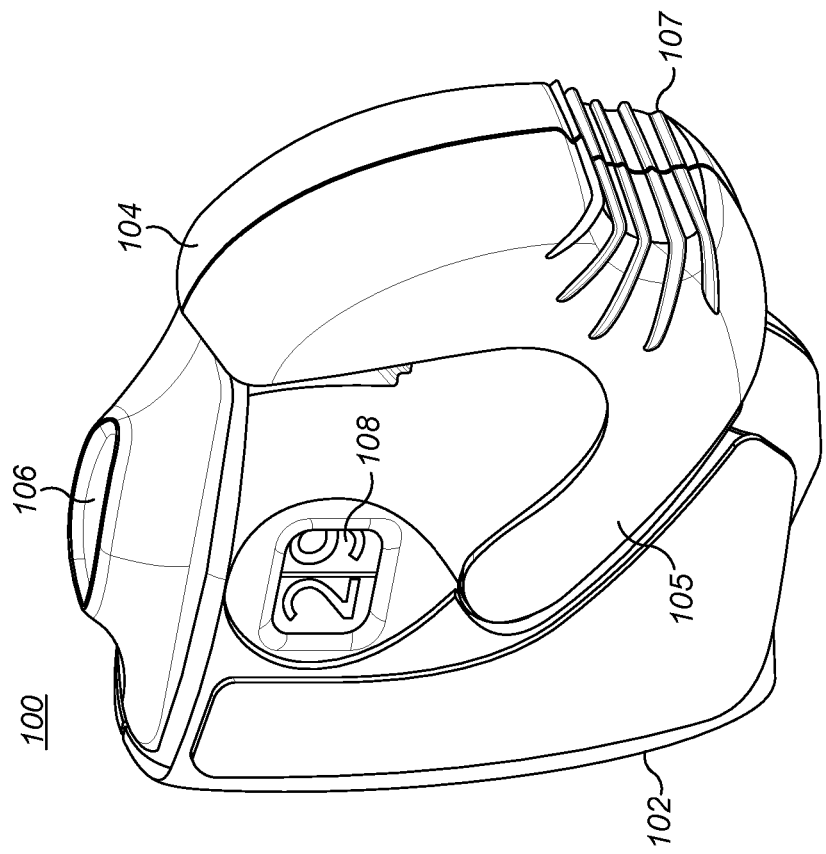
FIGS. 1A and 1B show an embodiment of a medicament delivery device according to the present invention.

In the following description and accompanying drawings, corresponding features of a medicament delivery device or its components may be identified using corresponding reference numerals. For clarity, not all of the features are labelled in every figure, though any unlabelled features may of course be cross-referenced against the corresponding figures in which they are shown labelled.

Figure 1A:
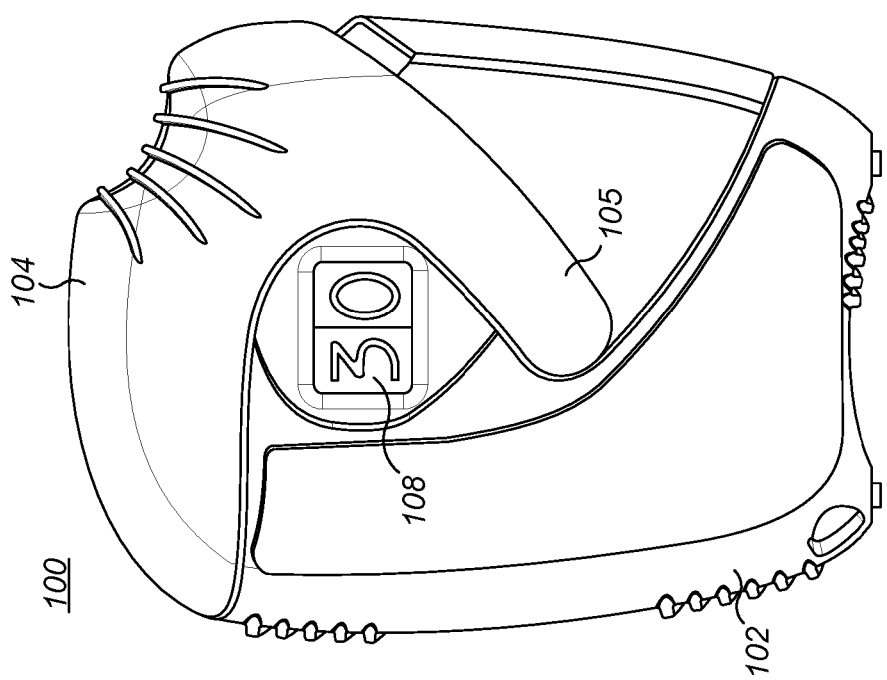

An embodiment of a medicament delivery device 100 according to the present invention is shown in FIGS. 1A and 1B. The device 100 comprises a generally rectangular housing 102. A movable mouthpiece cover 104 is pivotably coupled to the housing 102. The mouthpiece cover 104 has a pair of arms 105 via which it is coupled to the housing 102. The arms 105 are located at one end of the mouthpiece cover 104 and couple to the front and rear sides of the housing 102. The mouthpiece cover 104 may therefore be described as generally L-shaped. The arms 105 are pivotably coupled to the housing at a position roughly central to the housing 102. This allows the mouthpiece cover 104 to pivot about a corner of the housing 102.

The mouthpiece cover 104 can be moved from a closed position, shown in FIG. 1A, to an open position, shown in FIG. 1B, whereby a mouthpiece 106 of the device 100 is exposed. Once exposed, a user can inhale medicament from the device 100 via the mouthpiece 106. An indicator window 108 indicates the number of doses remaining in the device 100.

During movement from the closed position to the open position, the mouthpiece cover 104 actuates a drive mechanism within the device 100 that primes the device 100 by preparing a medicament dose contained therein for inhalation by a user of the device 100, as discussed further on. At the same time, the mouthpiece cover 104 actuates a counter mechanism, which reduces the number shown in the indicator window 108 by one unit accordingly. The displayed number indicates the number of doses remaining in the device 100.

Once a user has inhaled the medicament dose, the mouthpiece cover 104 can be moved back to the closed position to protect the mouthpiece 106. This helps to prevent contaminants from entering the device 100.

The mouthpiece cover 104 can be moved between closed and open positions when the device 100 is held in one hand of the user, with the user able to use their thumb or fingers to move the mouthpiece cover 104. The mouthpiece cover may be provided with a set of one or more protrusions 107, for example ridges, to help facilitate grip when moved by a user. The set of protrusions 107 on the device shown are located on the mouthpiece cover 104 near to a corner of the arm 105. Further sets of one or more protrusions (not shown) may be provided to facilitate grip on the underside of the housing 104, on the side of the housing 104, preferably including on the corner diametrically opposed to the corner of the housing 104 where the mouthpiece cover 104 provides protrusions 107 (as described above), when closed, and/or the unattached, free end of the mouthpiece cover 104 that moves open relative to the housing 104.

Figure 2B:
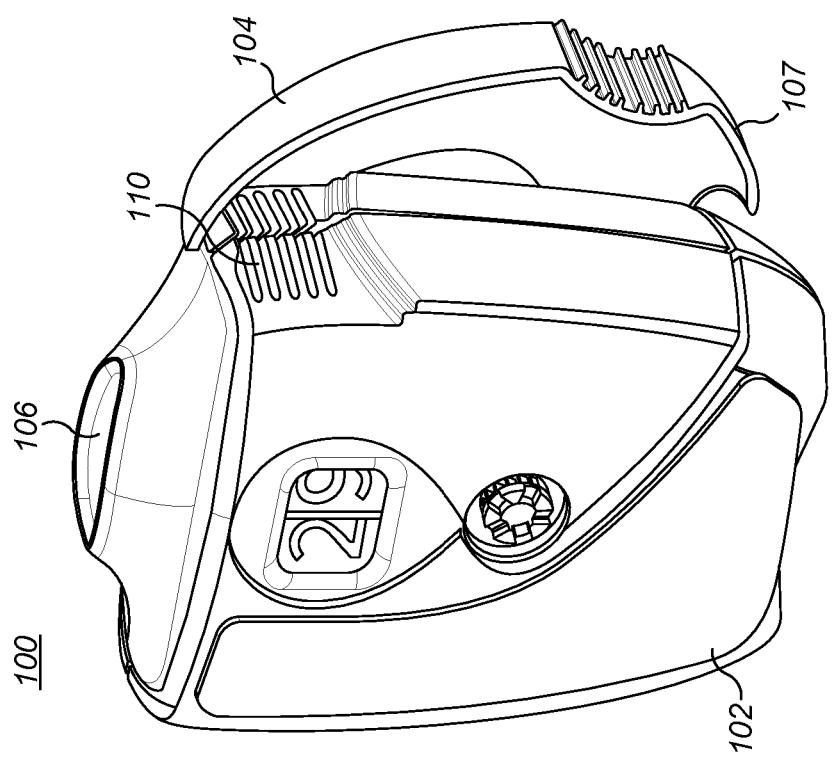
FIGS. 2A and 2B show the device of FIG. 1 with part of the mouthpiece cover cut-away.
Figure 2A:
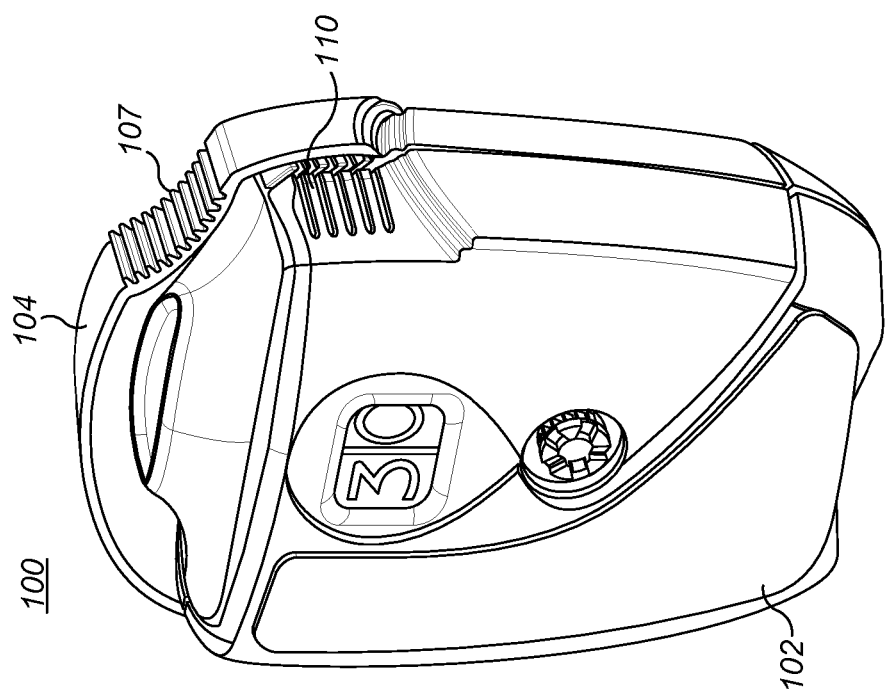

FIGS. 2A and 2B again show the device 100 with the mouthpiece cover 104 in the closed and open positions, respectively. A portion of the mouthpiece cover 104 has been omitted to show a vent 110 through which external air is drawn into the device 100 during an inhalation event. As can be seen, the vent 110 is covered by the mouthpiece cover 104 in both the closed and open positions. This provides the advantage that a user holding the device 100 cannot cover the vent 110 with their fingers or thumb during use, which would otherwise restrict the flow of air into the device 100.

Although it substantially covers the vent 110 at all times, the mouthpiece cover 104 does not provide an airtight seal with the housing 102 that would prevent air from being drawn into the device 100 when in the open position. There are sufficient gaps between the mouthpiece cover 104 and the housing 102 to allow sufficient air flow into the vent 110 when the mouthpiece cover 104 is in the open position.

Figure 3B:
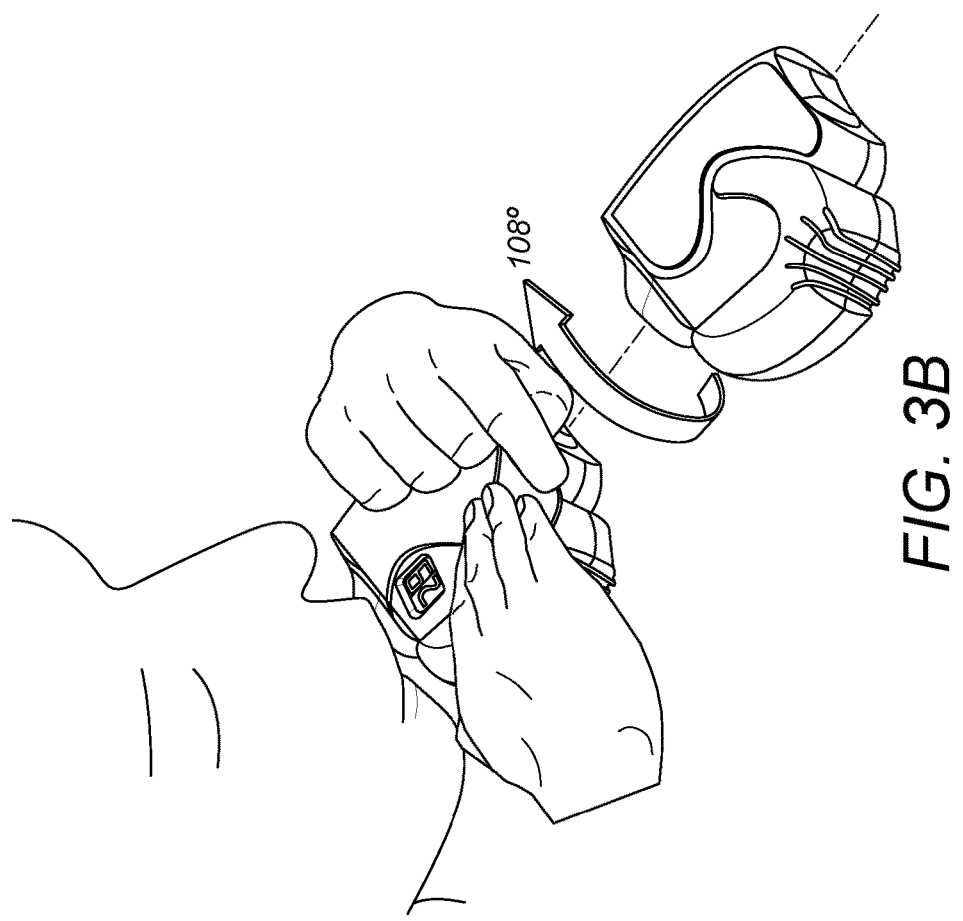
FIG. 3B shows the device in use.
Figure 3A:
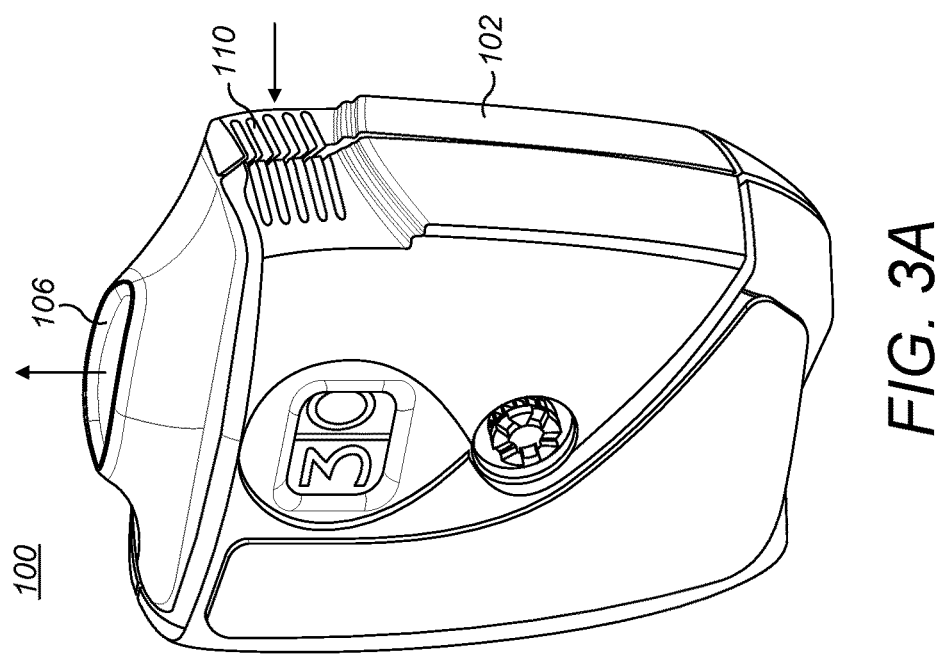
FIG. 3A shows the direction of airflow through the device (shown with the mouthpiece cover omitted) during inhalation by a user.

FIG. 3A shows the device 100 with the mouthpiece cover 104 omitted. Arrows are provided to show the direction of air flow during an inhalation by a user (e.g. an "inhalation event"). As a user inhales through the device 100, as illustrated in FIG. 3B, external air enters the housing 102 via the vent 110. The inhaled air is drawn along airpaths defined by a manifold arranged within the housing 102 (described further on) whereby it entrains a dose of medicament (i.e. aerosolises the medicament), before the aerosolised medicament (i.e. the medicament-laden air) exits the housing 102 via the mouthpiece 106 through which the user is inhaling. Advantageously, due to the particular configuration of the device 100 (as will be explained), it can be used in any orientation.

Figure 4:
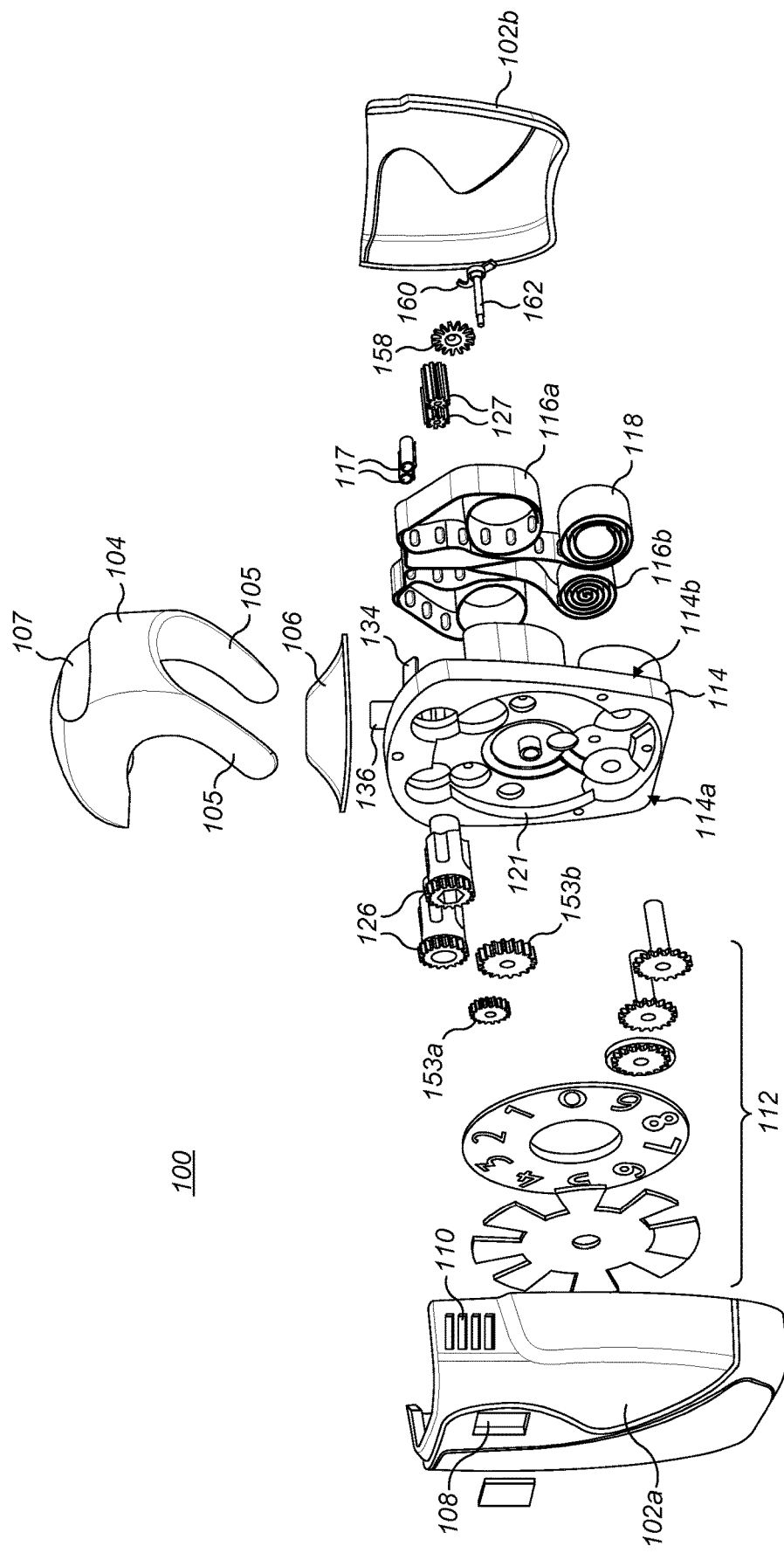
FIG. 4 shows an exploded view illustrating the components of the device.

An exploded view of the device 100 and its components, taken from a front perspective of the device 100, is shown in FIG. 4. The various components and their function will be described in detail further on; however, it is noted that the housing 102 generally comprises a front cover 102a and a rear cover 102b that join together to form the housing 102, and a main body (or "chassis") 114 that locates within the housing 102 between the front and rear covers 102a, 102b. The mouthpiece 106 locates onto the top of the main body 114, when assembled.

The main body 114 comprises a front body portion 114a and a rear body portion 114b, though only the front portion 114a is visible. A counter mechanism 112, which in this embodiment is a Geneva mechanism comprising a tens wheel 112a and a units wheel 112b, is shown arranged to locate into recesses 121 provided in the front portion 114a of the main body 114. The counter is used to indicate the number of doses remaining in the device 100 through the indicator window 108 provided on the front cover 102a of the housing 102, as mentioned above. A gear train is also provided as part of the drive mechanism.

Two medicament carriers 116a, 116b, each of which may contain a different formulation (e.g. of dry powder medicament) are shown arranged to locate between the rear body portion 114b and the rear cover 102b. The medicament carriers 116 define a "serpentine" path along which they travel within the device 100. The medicament carriers 116a, 116b each contain a plurality of compartments 118 spaced along a carrier strip 120 and sealed by a sealing layer 122. Each sealed compartment 118 contains a discrete dose of a medicament.

Figure 5B:
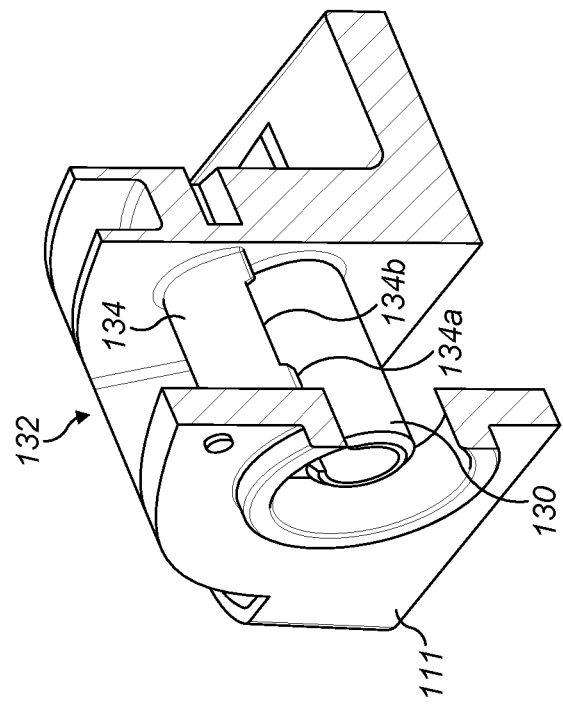
FIGS. 5A and 5B show the opening mechanism of the device.
Figure 5A:
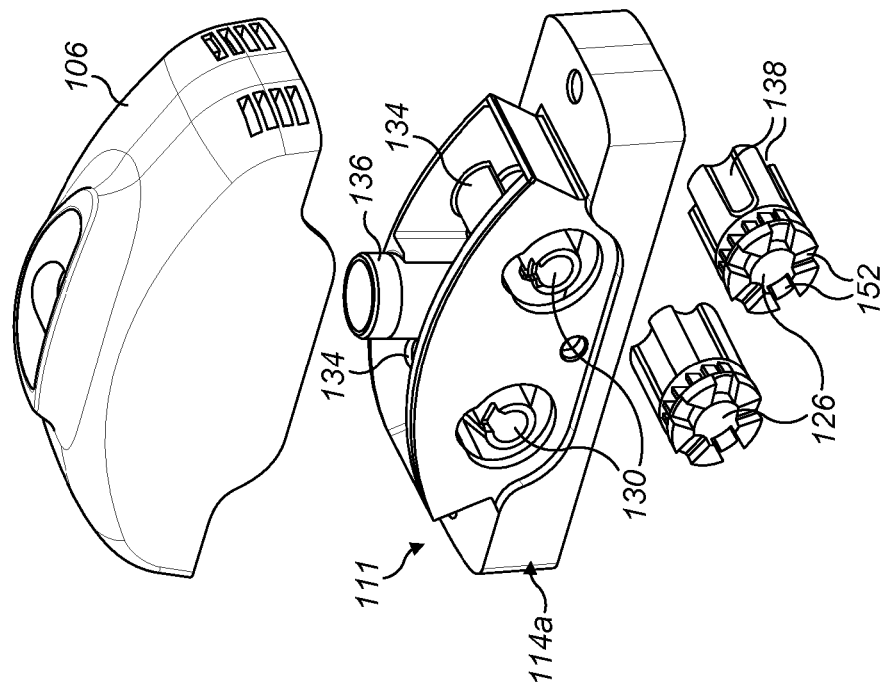

FIGS. 5A and 5B show, in more detail, a manifold 111 that provides part of an "aerosol engine" of the device 100. The manifold 111 forms part of the main body 114 shown in FIG. 4. It will be noted that FIG. 4 is only intended to be illustrative of the device 100 and its components, including the main body 114, and therefore does not show the manifold 111 in any detail. An inhalation chamber 136 extends out from the top of the manifold 111, over which the mouthpiece 106 is attached.

An opening mechanism 132 is provided to expose the discrete medicament doses that are sealed in the individual compartments 118 of each medicament carrier 116 as it is advanced (i.e. moved through the opening mechanism 132). Each opening mechanism 132 employs a release member 134 that is arranged to engage between the carrier strip 120 and sealing layer 122 whereby gradually to separate (e.g. to peel) the sealing layer 122 from the carrier strip 120 as the medicament carrier 116 is advanced through the opening mechanism 132 by an indexing mechanism 124. Each indexing mechanism 124 comprises an indexing wheel 126, which is mounted onto a bearing shaft 130. Each bearing shaft 130 is hollow such that air can pass through it, as will be described further on. The indexing wheels 126 are shown dismounted from the bearing shafts 130 in FIG. 5A.

Each indexing wheel 126 is generally cylindrical, and has a plurality of recessed indentations, or slots 138, regularly spaced around its circumference. Each slot 138 is configured to receive a transversely-orientated compartment 118 of the medicament carrier 116. The slots 138 are therefore shaped to correspond with the shape of the external surface of the compartments 118. This ensures that the compartments 118 fit snuggly (e.g. are received) within the indentations 138 of the indexing wheels 126 which enables the indexing wheels 126 to pull the medicament carrier 116 efficiently through the release member 134.

For ease of explanation, various components of the device 100, such as the arrangement of opening mechanisms 132 and release members 134 may be described in the singular in certain parts of the following description, for example in relation to their configuration and use with a single medicament carrier 116. It will, of course, be appreciated however that where the device 100 contains two of the same component, each component (e.g. the opening mechanism 132 and release member 134) will have a similar configuration. In particular, while aspects described herein may be applied to a medicament delivery device arranged to handle only a single medicament carrier, the exemplary device 100 described herein is arranged to handle two separate medicament carriers 116, and therefore contains two opening mechanisms 132, two release members 134, etc.

The indexing wheel 126 is caused to rotate as the device 100 is primed (e.g. by moving the mouthpiece cover 104 to the open position), and rotation of the indexing wheels 126 causes the medicament carrier 116 to advance, thereby moving the next compartment 118 into an "entrainment" position, as will be discussed further on.

As the indexing wheel 126 is rotated, it advances the medicament carrier 116 through the opening mechanism 132. The release member 134 is positioned immediately adjacent the indexing wheel 126, such that the compartments 118 are opened during their engagement with the release member 134 while retained within a slot 138 of the indexing wheel 126. Providing the indexing wheel 126 with discrete indentations 138 in which the compartments 118 are received helps to ensure that each compartment 118 is in correct alignment with the release members 134. The indexing wheel 126 is rotated one indentation 138 at a time, such that each compartment 118 is fully aligned with the release member 134, one at a time, sequentially.

It is important to ensure that the release member 134 is correctly engaged with the medicament carrier 120, between the carrier strip 120 and the sealing layer 122 to facilitate good separation of the sealing layer 122 from the carrier strip 120. It is also important to ensure accurate positioning of the medicament carrier 116 relative to the release member 134 to ensure that the medicament dose contained within a compartment 118, which is exposed by removal of the sealing layer 122, is subsequently contained within the compartment 118, at least temporarily, by the release member 134.

The portion of medicament carrier 116 having unopened compartments 118 is initially stored within the housing 102 in a coiled up configuration, as can be seen later in FIG. 12A, for example.

The release member 134 is shown having a curved top surface, and furthermore describes a generally C-shaped cross-sectional profile. As such, the underside of the release member 134 (e.g. a side of the release member arranged to face the carrier strip 120) generally conforms to the curvature of the indexing wheel 126. At least one surface (i.e. the topside and/or underside) of the release member 134 should be curved in order to provide relative curvature between its upper and lower surfaces, thereby to promote separation of the sealing layer 122 from the carrier strip 120 of the medicament carrier 116.

The release member 134 is arranged to extend across substantially the entire width between the carrier strip 120 and sealing layer 122 of the medicament carrier 116. Thus, as will be understood from FIG. 6, as the medicament carrier 116 is advanced through the opening mechanism 132, a separated portion of carrier strip 120 will pass underneath (i.e. across the underside of) the release member 134 and a separated portion of sealing layer 122 will pass across the topside of the release member 134.

The release member 134 has a leading edge 134a (i.e. a front edge of the release member 134 that engages with the medicament carrier, in use) that is configured to form a "blade" portion that engages between the carrier strip 120 and sealing layer 122 to urge them apart, for example. The raised profile of the release member 134 (i.e. curved upper surface) helps facilitate separation of the sealing layer 122 from the carrier strip 120.

The release member 134 includes a recessed portion or cut-out ("slot") 134b along its leading edge 134a to inhibit medicament being retained between the release member 134 and the carrier strip 120 as the medicament carrier 116 is advanced. This configuration can improve drug delivery performance and consistency of dose delivery through the lifespan of the device 100. Thus, the slot 134b provides a gap between the leading edge 134a and a carrier strip 120 over the compartments 118. This gap can allow medicament that was adhered to the sealing layer 122 to be aerosolised, rather than wasted. Preferably, in the region of the slot 134b, the leading edge 134a curves upwardly from the lower surface to meet the upper surface of the release member 134.

The slot 134b in the leading edge 134a of the release member 134 should extend as far across the width of the compartment 118 as possible to maximise the effect, but preferably without extending the entire width of the release member 134, to ensure stability of opening and to control the point at which the sealing layer 122 separates from the carrier strip 120 ahead of the release member 134, which can affect the entrainment position, and may also cause air leaks.

The manifold 111 has two separate opening mechanisms 132, each with a respective release member 134. This arrangement means that two different medicament carriers 116 can be handled at once such that their respective doses of medicament can be released at the same time. This is beneficial if the two medicament formulations are not stable when mixed.

As mentioned above, as the medicament carrier 116 is advanced through the opening mechanism 132 by the indexing mechanism 124, the next compartment containing medicament is moved into an "entrainment position". As the medicament carrier 116 is advanced, the release member 134 separates the sealing layer 122 from the carrier strip 120 thereby opening that compartment 118 to expose the medicament dose contained therein. However, in the "entrainment position", the opened compartment 118 is positioned adjacent the release member 134, such that the release member 134 covers the opened compartment 118, thereby containing the medicament exposed by the removal of the sealing layer 122, as shown in FIG. 6.

Figure 6:
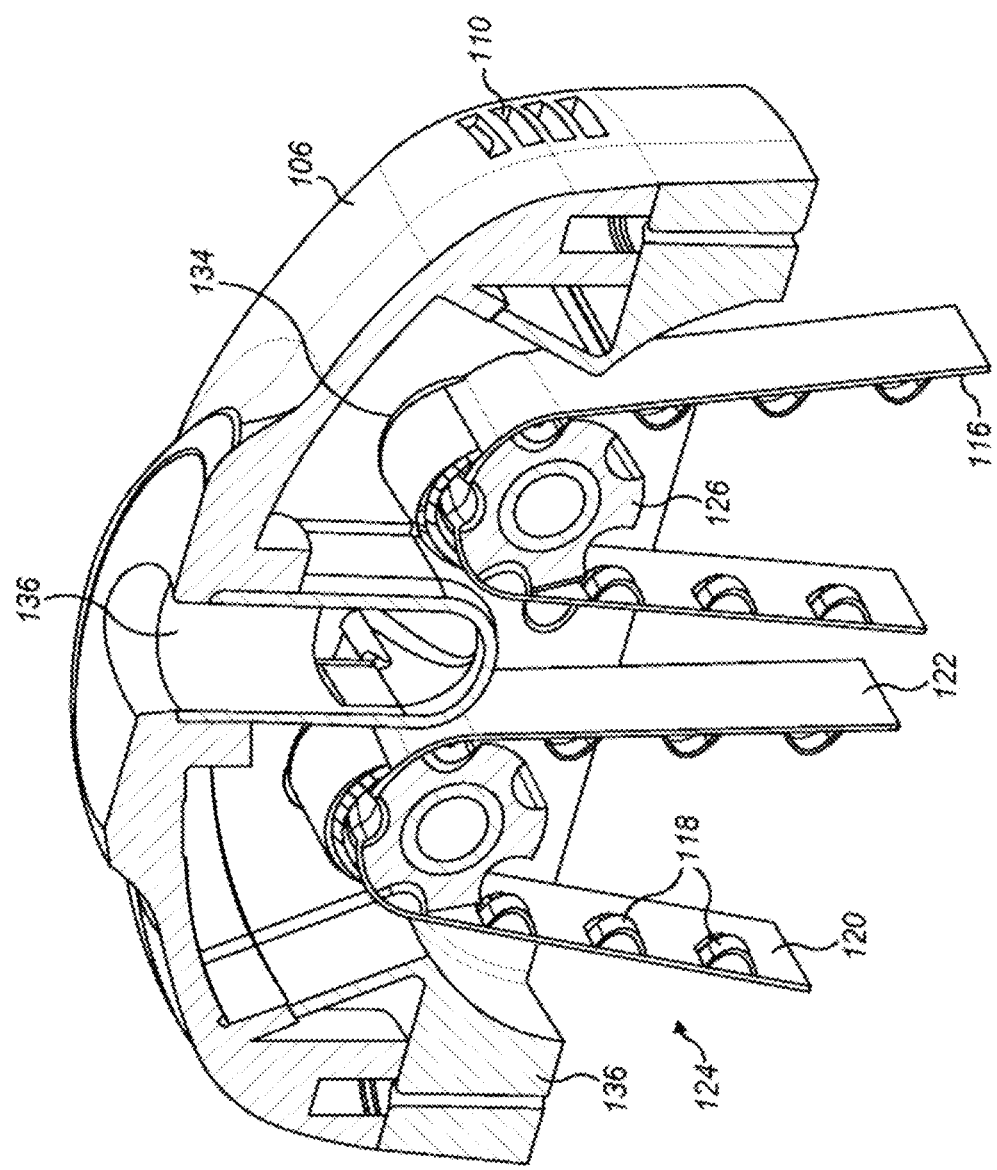
FIG. 6 shows the indexing mechanism of the device.

FIG. 6 is a sectional view of the device 100 showing the indexing mechanism 124 in more detail. Each indexing wheel 126 is engaged with a medicament carrier 116 via engagement of the slots 138 of the indexing wheels 126 with compartments 118 of the medicament carrier 116, whereby to advance the medicament carrier when rotatably driven. Each medicament carrier 116 is further engaged with a respective opening mechanism 132, as described above, such that an opened compartment of each carrier strip 120 is in the "entrainment position", i.e. adjacent the release member 134, such that the release member 134 covers the opened compartments 118, thereby containing the medicament exposed by removal of the sealing layers 122. The inhalation chamber 136 is shown extending through the mouthpiece 106.

For simplicity, as mentioned above, one only of the opening mechanisms 132 may be referred to, though it will be appreciated that the description can relates to each of the pair of opening mechanisms 132 shown.

The release member 134 is arranged adjacent the indexing wheel 126 to bring the medicament carrier 116 into contact with the release member 134. As such, the underside of the release member 134 is curved substantially to conform to the curvature of the indexing wheel 126. The radius of curvature of the release member 134 is therefore, ideally, similar to that of the indexing wheel 126 such that the release member 134 can be positioned close to the indexing wheel 126, as shown in FIG. 6. This arrangement may provide a more compact device overall.

Thus, as the medicament carrier 116 is advanced by the indexing wheel 126 when the device is primed, movement of the medicament carrier 116 relative to the release member 134 causes the sealing layer 122 gradually to separate from the carrier strip 120, in a peeling fashion due to the insertion of the release member 134. As the medicament carrier is advanced, the carrier strip 120 passes below (i.e. below the release member 134) and the separated sealing layer 122 passes over (i.e. above the release member 134). Once past the release member 134, the carrier strip 120 and sealing layer 122 of each medicament carrier 116 may be brought back together to be stored (e.g. coiled together) at a later stage, for example such that the used part of the medicament carrier 116 can advantageously be stored on the same (i.e. a single) spool 129 (as shown in FIG. 14A) or in the same compartment. Alternatively, the separated carrier strip 120 and sealing layers 122 may be stored separately, for example on separate spools (not shown).

Around the end face of each indexing wheel 126, which is the portion of the indexing wheel 126 facing out of the page, are provided cut-outs 152, equal in number to the number of slots 138 and aligned with the respective slots 138. In the embodiment shown, each indexing wheel 126 has five slots 138 and five corresponding cut-outs 152 in its end face. Each cut-out 152 allows air to flow through the hollow interior of the indexing wheel 126 and to pass up to its respective slot 138.

Advantageously, when the compartments 118 are in the entrainment position, following removal of the sealing layer 122, the release members 134 cover the compartments 118 so as substantially to contain the medicament dose in the compartments 118. This containment is not completely airtight, however, as the release members 134 form part of an entrainment airpath, via which the contained medicament dose is aerosolised, as will be explained further on.

Figure 7B:
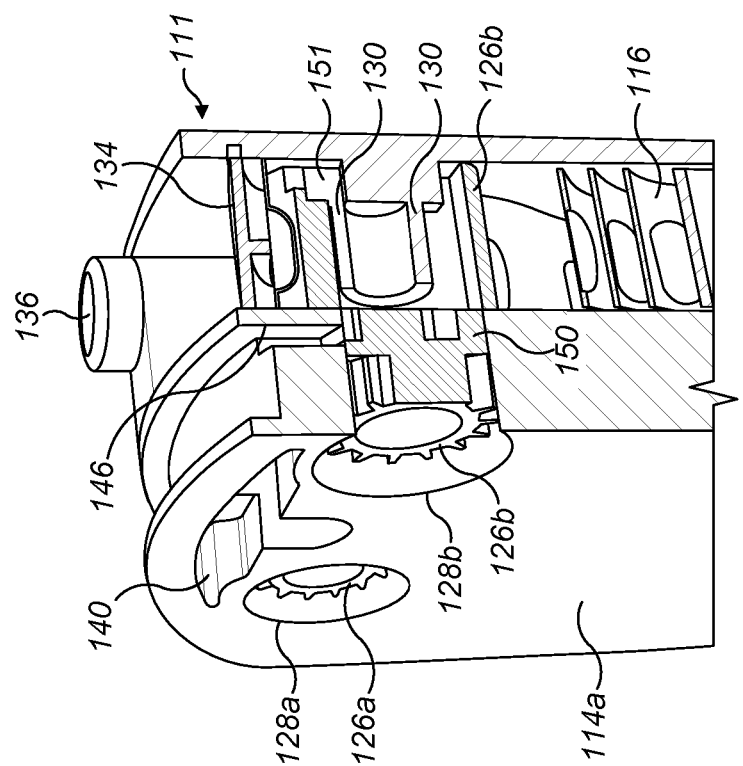
FIGS. 7A and 7B show aspects of the manifold of the device.
Figure 7A:
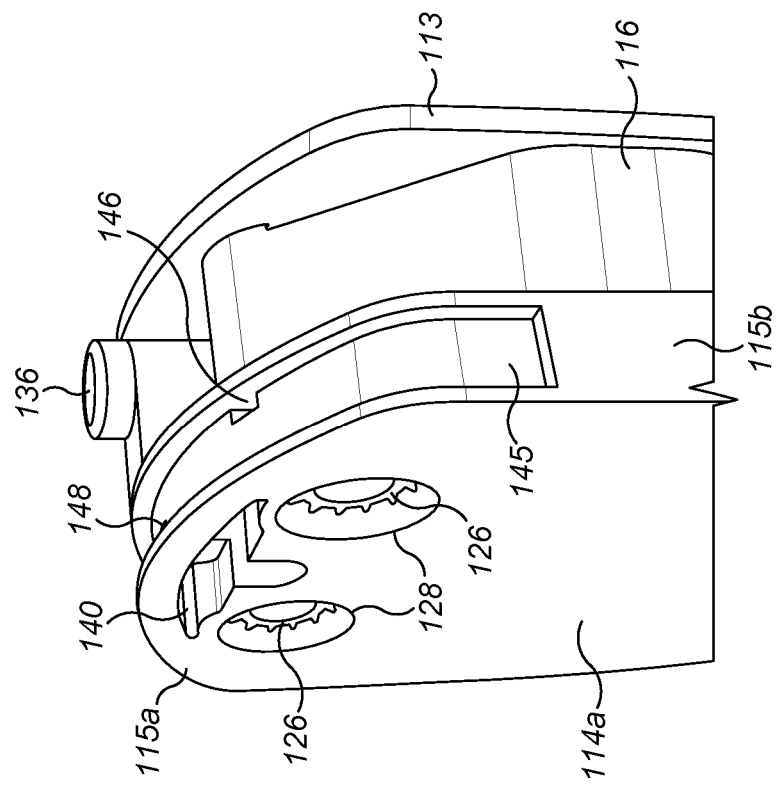

FIGS. 7A and 7B show a more detailed view of the upper portion of the main body 114, including the manifold 111. It will be appreciated that the FIGS. 7A and 7B, and FIGS. 8A and 8B are illustrative simply to show the interaction of the components in the manifold 111. Two indexing wheels 126a, 126b are located, in corresponding holes 128a, 128b, in the front body portion 114a such that they extend through the main body 114. A medicament carrier 116a is also shown engaged by one of the indexing wheels 126a. As noted above, in use, each indexing wheel 126 is rotatably driven to advance its respective medicament carrier 116 into an "entrainment position" when the device 100 is primed (i.e. when the mouthpiece cover is moved to its open position). An air mixing chamber 140 is provided on the outer side of the front body portion 114a, in which "entrained air" (i.e. medicament-laden air) is mixed with bypass air prior to being inhaled via the inhalation chamber 136.

As can be seen, a channel 145 is formed in the top of the front body portion 114a, extending between opposing sides 115a, and 115b of the front body portion 114a. The channel 145 is located across the top of a front body portion 114a. The channel 145 passes over the two indexing wheels 126, and may therefore be described as "bridging" over the indexing wheels 126. The channel 145 forms part of both an entrainment airpath 142 and a bypass airpath 144, along which air drawn in through the vent 110 flows during inhalation. An entrainment port 146 and a bypass port 148 are both provided in the channel 145. The bypass port 148 feeds air drawn through the device 100 directly into the mixing chamber 140, and forms a further part of the bypass airpath 144. Air drawn along the bypass airpath 144 can therefore be described as "bypass air".

The entrainment port 146 feeds air into the manifold 111 where it entrains the medicament and is therefore part of the entrainment airpath 142, as will be described below. This air may therefore be described as "entrainment air".

In use, air flows through the entrainment port 146, through the indexing wheel 126 and bearing shaft 130 and emerges the distal side of the release member 134, on the underside of the release member 134 (e.g. a side of the release member arranged to face the carrier strip 120). The air then passes along the underside of the release member 134, along which path it is directed into an opened compartment 118 retained by the indexing wheel 126, such that the flowing air entrains the exposed dose of medicament. The entrained air then passes out of the compartment 118 and back along the underside of the remaining portion of the release member 134 towards the channel 145 and then passes into a mixing chamber 140, where it is mixed with bypass air to de-aggregate the entrained medicament.

An exemplary embodiment can be described with reference to FIG. 7B. Each indexing wheel 126 is rotatably mounted on its respective hollow bearing shaft 130. Each bearing shaft 130 is mounted at its base to the rear body portion 114b. The bearing shaft 130 extends out from the rear body portion 114b, perpendicularly, towards the front body portion 114a. Each bearing shaft 130 is hollow to provide an airpath. Each indexing wheel 126, having a hollow through-bore, is mounted on its bearing shaft 130 so that its base (or "distal") end, in which are provided the cut-outs 152, coincides with the base of the bearing shaft 130. The other end of the indexing wheel 126 may therefore be referred to as its "proximal" end. A notch is provided at the base of the bearing shaft 130. Thus, when the medicament carrier 116 is in the entrainment position, one of the cut-outs 152 in the end face of the indexing wheel 126 will be aligned with the notch in the bearing shaft 130 to provide an airpath from the bearing shaft 130 to the release member 134.

A groove 150 extends around an inner portion on the indexing wheel 126, the groove 150 being aligned with the entrainment port 146 when the indexing wheel 126 is mounted on the bearing shaft 130. The groove 150 (e.g. and therefore also the indexing wheel 126) is further arranged to provide an airpath that connects the exterior of the indexing wheel 126 to the interior of the indexing wheel 126 (i.e. its hollow through-bore). Thus, the groove 150 also provides an airpath between the entrainment port 146 to the bearing shaft 130 when the indexing wheel 126 is mounted thereon. The groove 150 is aligned with the entrainment port 146 such that air flowing along the channel 145 is drawn through the entrainment port 146, through the groove 150 and into the bearing shaft 130. From the bearing shaft 130, the air passes through a notch 151 at the distal end of the bearing shaft 130, and arrives at a distal end of the release member 134 (i.e. relative to the channel 145). This combined airpath forms part of the "entrainment airpath" 142, as shown in FIGS. 8A and 8B, with arrows provided to illustrate the direction of air flow along the airpath 142.

Figure 8A:
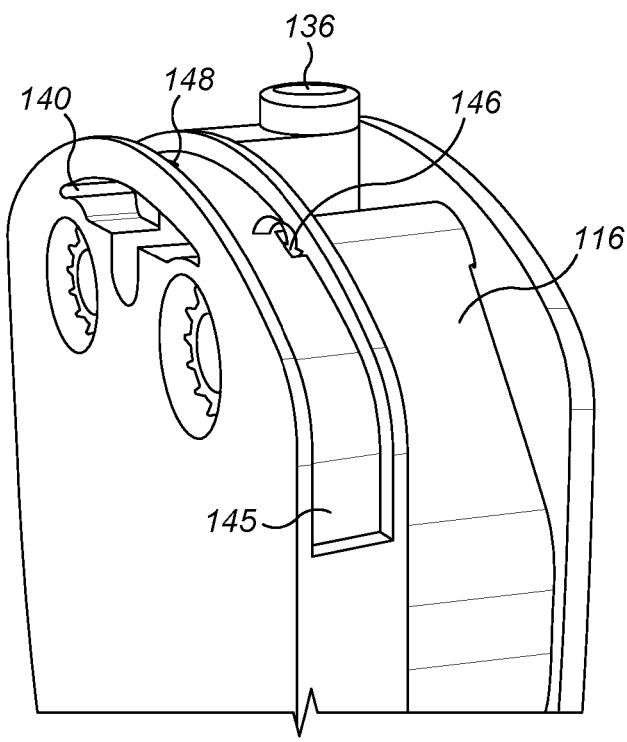
FIGS. 8A and 8B show an "entrainment" airpath through the manifold.
Figure 8B:
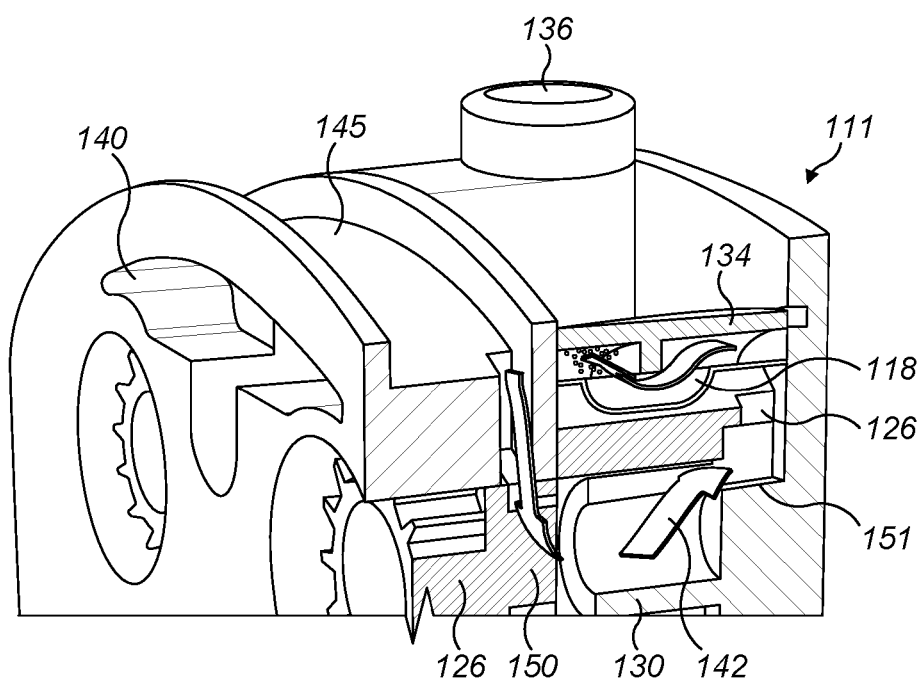
Figure 9A:
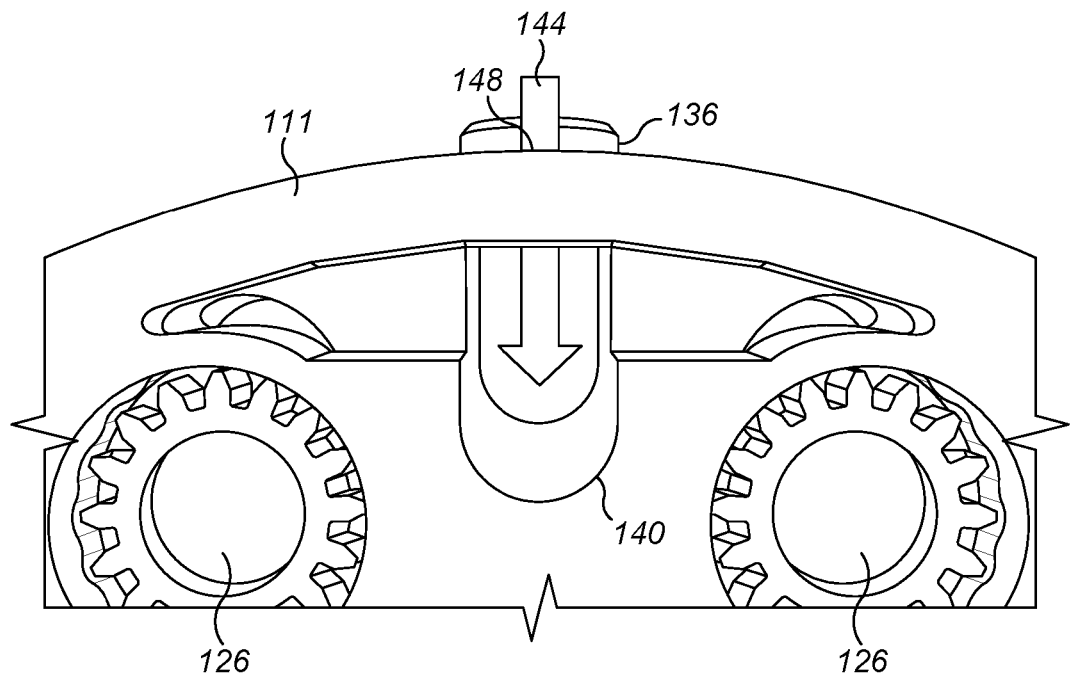
FIGS. 9A and 9B show an inhalation chamber of the device in which the "entrainment" airpaths mix with a "bypass" airpath.
Figure 9B:
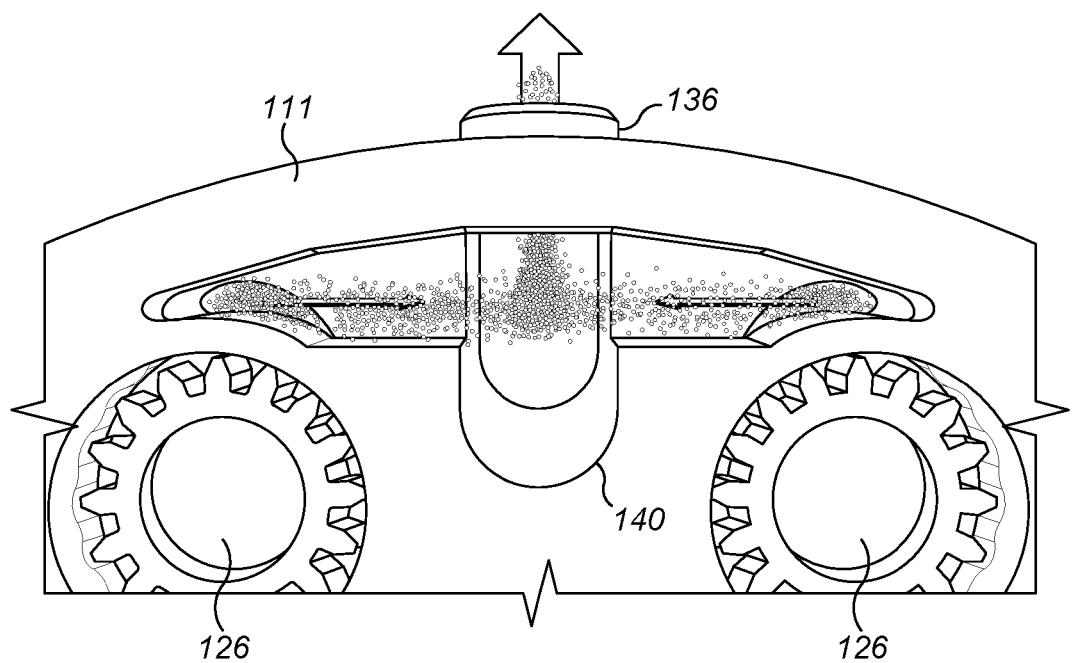

FIGS. 8A and 8B show essentially the same aspects of the device as FIGS. 7A and 7B, with the addition of arrows showing the air path of the entrainment air entering the entrainment port 146 along the entrainment airpath 142, and passing through the manifold 111 to entrain the medicament doses. The entrainment of each dose of medicament from an opened compartment is shown in FIG. 8B. The release member 134 is positioned adjacent (i.e. above, in this orientation) the indexing wheel 126 mounted on the bearing shaft 130. An opened compartment 118 of a medicament carrier 116 is shown in the entrainment position (i.e. adjacent—or below, in this orientation—the release member 134), retained within the indentation 128 of the indexing wheel 126, for illustrative purposes. The release member 134 is cut-away in this view but one of skill will appreciate that the compartment 118 has been opened by the release member 134 during advancement of the medicament carrier 116 to the entrainment position, as described above, such that the medicament in the compartment 118 is exposed.

Figure 10A:
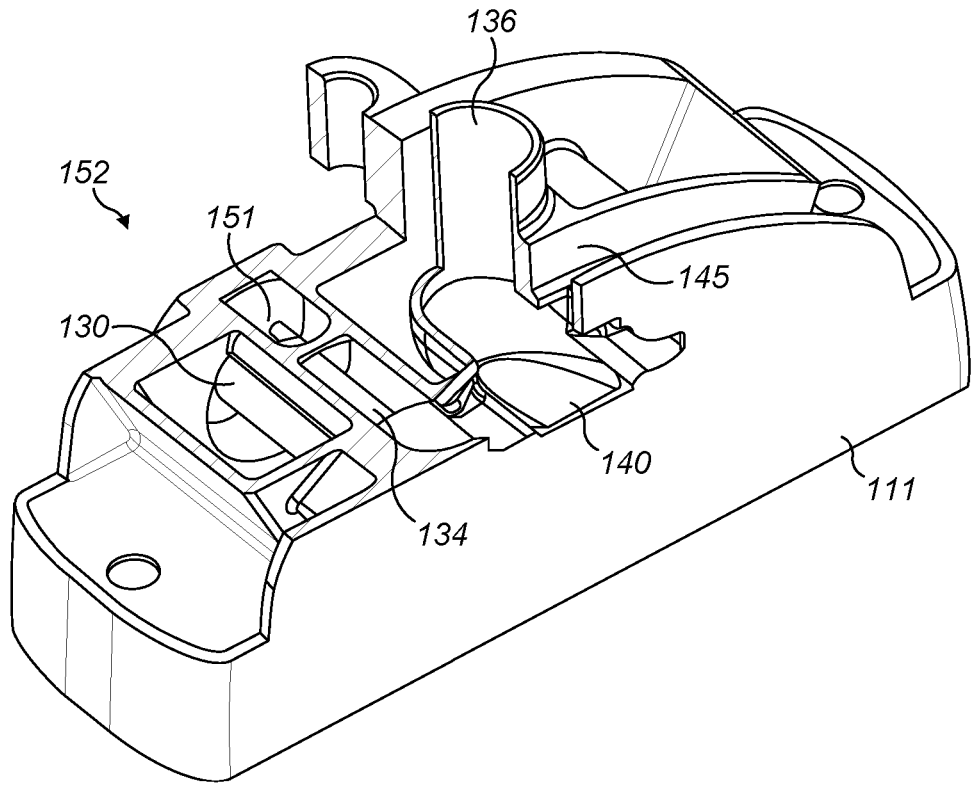
FIGS. 10A and 10B show sectional views of the device manifold.
Figure 10B:
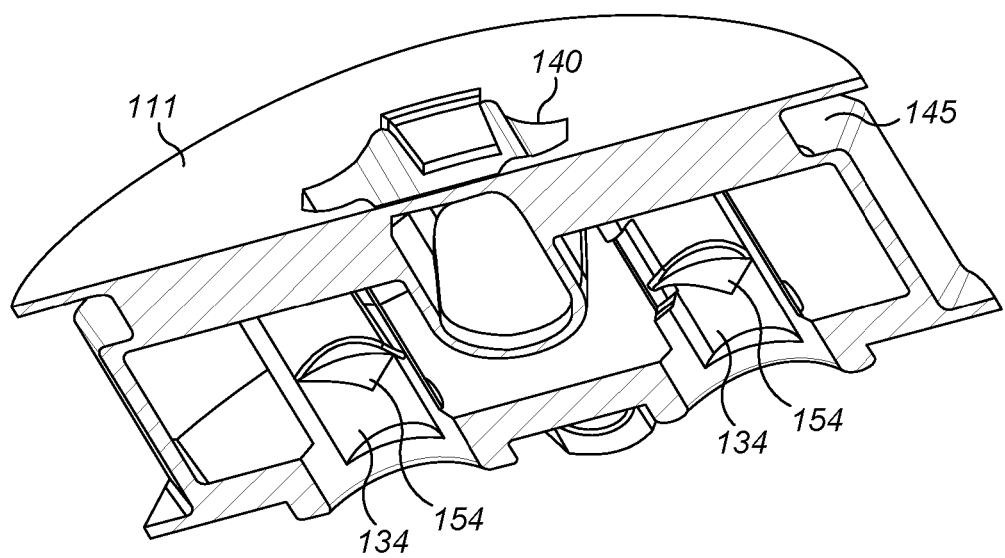
Figure 11:
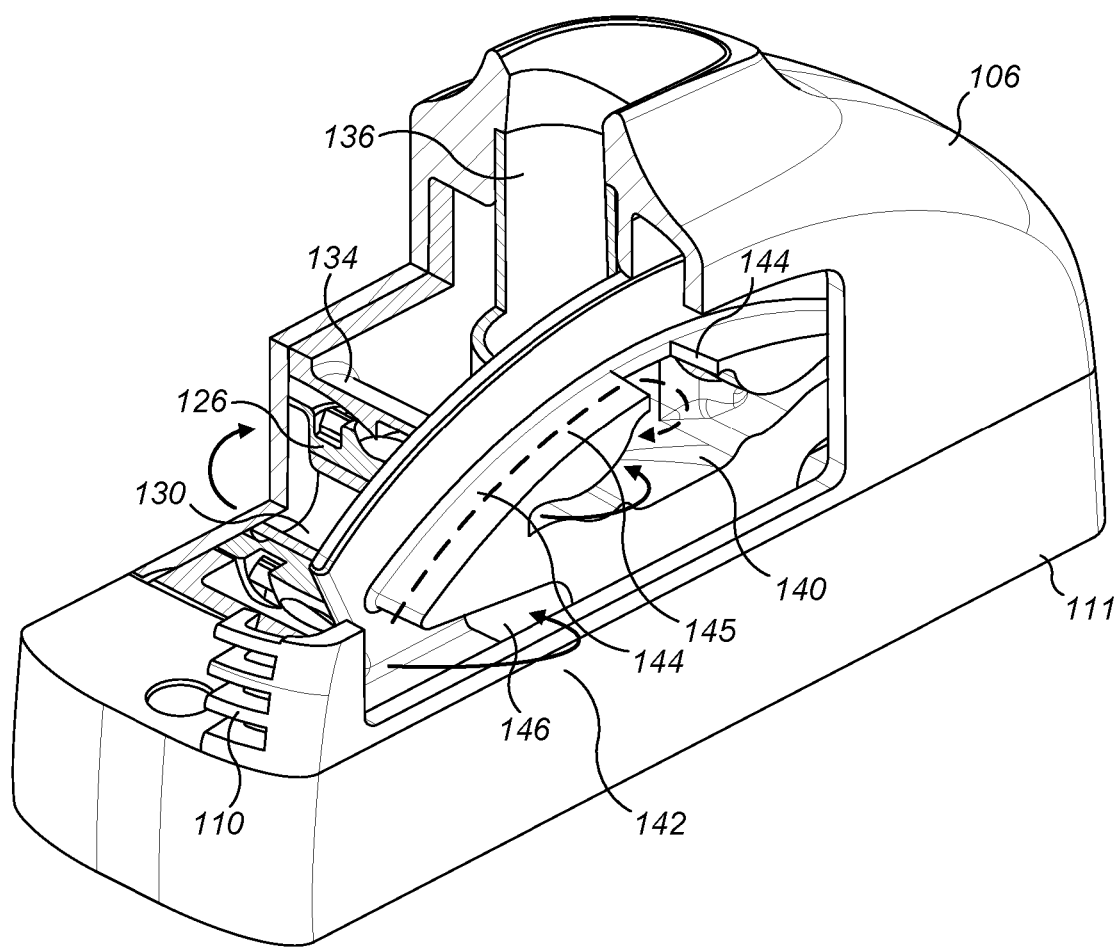
FIG. 11 shows an alternative configuration of a device manifold.

The release member 134 has a conditioning member 154 (or "feature"), located on an underside surface of the release member 134 (e.g. a side of the release member 134 that faces the carrier strip 120), as can be seen later in FIG. 10B. The conditioning member 154 acts to interrupt the flow of entrainment air, and to direct it from the distal end of the release member 134 into the opened compartment 118, as it passes across (the underside surface of) the release member 134, rather than simply allowing it to flow across the release member 134. The conditioning member 154 may be configured to condition the flow of air and/or direct air into the opened compartment 118, preferably to increase flow velocity and/or vorticity of the air. The conditioning member 154 may also comprise one or more vortex shedding features.

As the entrainment air passes through the opened compartment 118, it entrains the medicament dose contained therein. The medicament-laden entrainment air then continues to pass along the release member 134 towards the proximal end of the release member 134 and on to the mixing chamber 140 though an outlet port, which also forms part of the entrainment airpath 142. The direction of the air flow through the indexing wheel 126 and along the surface of the release member 134 may therefore be said to be in opposed directions, the air flowing in a first direction through the indexing wheel 126 and in a second direction along the surface of the release member 134. The entrainment airpath may therefore be said to "return" along the release member 134

Thus, the opening mechanism 132 is arranged to open a compartment 118 of the medicament carrier 116, as it is advanced through the opening mechanism 132, by way of a release member 134 configured to engage between the carrier strip 120 and the sealing layer 122 such that the sealing layer 122 is separated from the carrier strip 120 during advancement of the medicament carrier 116 into an entrainment position. Furthermore, the entrainment airpath 142 is arranged to direct air, via the release member 134 of the opening mechanism 132, into the opened compartment 118 when the medicament carrier 116 is in the entrainment position so as to entrain the medicament dose contained therein, wherein the release member 134 is arranged to provide part of the entrainment airpath.

As noted above, the entrainment air entering the mixing chamber 140, shown in FIG. 9A, merges with the bypass air that was drawn along the bypass airpath 144 as it enters the inhalation chamber 136 (or at least immediately prior), as shown in FIG. 9B, from which the mixture is inhaled by a user during an inhalation event. FIGS. 10A and 10B show sectional views of the manifold 111. As described above, entrainment air passes through the bearing shaft 130, entering via the entrainment port 146, and on to the release member 134 via the aligned notch and groove 150 in the end of the indexing wheel 126. The entrainment air then passes back along the (underside) surface of the release member 134 to entrain the medicament contained in an opened compartment 118, before mixing with bypass air in the inhalation chamber 140, as described above.

The conditioning member 154 can be seen located on the underside of the release member 134 so as to disrupt the flow of air across the release member 134 and direct it into an opened chamber 118. The conditioning member 154 (positioned in the entrainment airway passing through the release member 134) is shaped to increase the velocity (and potentially the vorticity) of the air which is directed into an opened compartment 118, and thereby improve evacuation of the compartment 118.

The mouthpiece 106 may be formed from a single, unitary, piece of plastic. The mouthpiece 106 is used to close off the airpaths in the aerosol engine. Air is routed through the centre of the indexing wheels 126, then directed back out and across the release member, which extends the full width of the medicament carrier 116. The release member 134 then directs the entrainment air through the opened compartment 118, entraining the medication contained therein. The drug-laden entrainment air is then directed into the bypass air, where they mix, before the mixed air is directed out of the device 100 via the mouthpiece 106.

The embodiments shown in the figures depict manifold arrangements in which the entrained air streams that have passed through exposed compartments 118 of different medicament carriers 116 are mixed together in a mixing chamber 140 and/or inhalation chamber 136 prior to exiting the device, in addition to mixing with bypass air. However, in other embodiments (not shown) the entrained air from different compartments 118 may be kept separate until exiting the device 100 downstream of the mouthpiece 106, for example in a user's mouth. The entrained air will of course still be mixed with bypass air. A mixing chamber 140 may optionally be provided for mixing each stream of entrained air with bypass air, but the mixing chamber 140 would be partitioned to keep the respective air streams separate. Similarly, the inhalation chamber 136 may be partitioned such that the entrained air streams are kept separate. Advantageously, the device 100 described herein results in a small number of components that constitute the airpaths, of which all but one component already has another function within the device.

FIG. 11 shows an example of a manifold 111 having a slightly different configuration to what is described above. This alternative manifold 111 is arranged to provide an aerosol engine that is essentially the same in structure and function as the embodiment of the above-described manifold, though rather than an entrainment port 146 being provided in the channel 145, the entrainment port 146 is instead located in the side of the front body portion 114*a*, such that the entrainment airpath passes underneath the channel 145. Similar to as described above, entrainment air enters the bearing shaft 130, and then passes up to the release member 134 via the aligned notch and groove 150 in the end of the indexing wheel 126. The medicament of an opened compartment 118 is entrained, and then mixed with bypass air, as described above.

FIG. 12A shows the front body portion 114*a*, and also the front cover 102*a*, the mouthpiece 106 and the mouthpiece cover 104. The indexing mechanism 124 can be seen with the medicament carriers 116 arranged to follow their designated paths. The drive mechanism 101 of the device is exposed, which is driven by movement of the mouthpiece cover between its closed position and open position, and back again to its closed position.

In the device shown, a (resiliently flexible) drive arm 160 is connected to a drive shaft 162 of the mouthpiece cover such that rotation of the mouthpiece cover rotates the drive arm 160 via the drive shaft 162. The drive arm 160 engages an idler gear 158 which in turn drives a pair of toothed drive wheels 127, via direct engagement with a first toothed drive wheel 127*a* that is rotatably connected to drive a second toothed drive wheel 127*b*. The pair of toothed drive wheels 127 are arranged to rotate in opposite directions to provide tension to the sealing layer 122 of the medicament carrier 116 while also driving rotation of the indexing wheels 126, thereby to advance the medicament carrier 116 through the respective opening mechanisms 132, as will be described in more detail below.

In this example, the idler gear 158 also provides a backlash mechanism, together with a separate pivotal latch arm 109, to inhibit backlash in the toothed drive wheels 127 once a compartment 118 has been advanced into an entrainment position. The latch arm 109 is arranged to engage with the idler gear 158 in a ratchet configuration that prevents counter-rotation of the idler wheel 158 once the medicament carrier 116 has been advanced into its entrainment position.

Figure 12B:
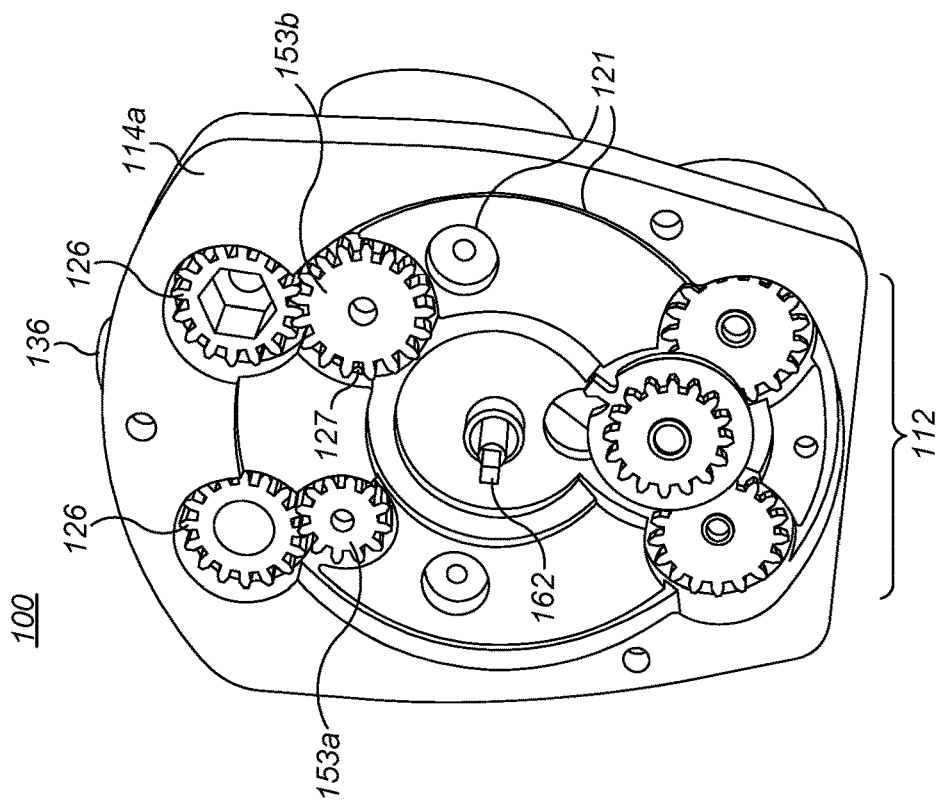
FIGS. 12A and 12B show front and rear views of the device chassis with components mounted thereto.
Figure 12A:
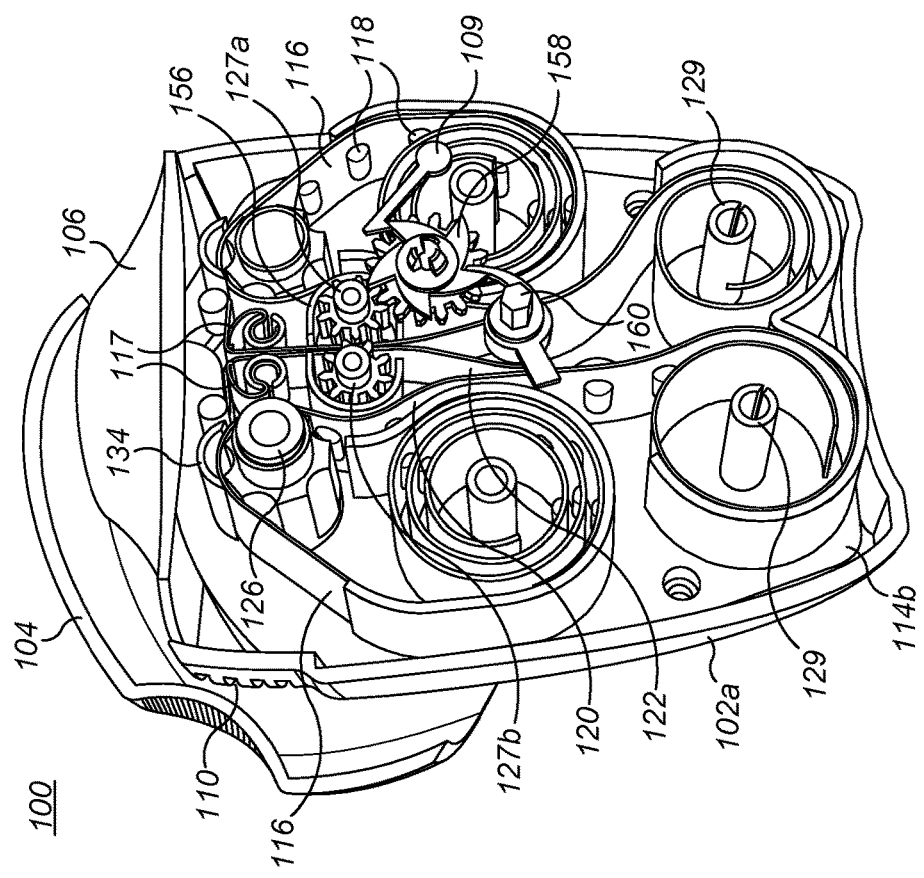

FIG. 12B, shows the rear body portion 114b, and in particular part of the gear train that drives both the indexing wheels 126 of the indexing mechanism, and the counter mechanism 112. A central gear wheel, which may itself provide part of the Geneva mechanism of the counter mechanism 112 (e.g. the units wheel) is absent from the centre of the gear train, though the drive shaft 162 that is connected to the mouthpiece cover 104, when assembled, is shown.

Two idler gears 153 are provided in the gear train to couple the drive wheels 127 (one of which is just about visible in FIG. 12B) with the indexing wheels 126. The idler gears ensure that each the indexing wheel 126 rotates in the same direction as the respective drive wheel 127a, 127b to which it is rotatably coupled. One of the idler gears 153b is larger than the other idle gear 153a, and its axis of rotation is offset further from the drive wheel 127 and indexing wheel 126 than that of the other idler gear 153a, such that the larger idler gear 153b can drive rotation of the counter mechanism 112 via the central gear (that is absent from FIG. 12B).

A retaining plate (not shown) may be provided to help retain the gear train that drives the counter mechanism 112 and indexing mechanism 124 in position within their respective recesses 121 provided in the rear portion 114b. The retaining plate can be arranged to secure to the main body 114, for example by tabs provided around the edge of the retaining plate that locate into corresponding receiving slots provided in the rear portion 114b of the main body 114.

FIGS. 13A to 13D illustrate the sequence of movement of the mouthpiece cover and the related movement of the drive mechanism and backlash mechanism as the mouthpiece cover 104 is moved from its closed position to its open position, and back again.

Figure 13B:
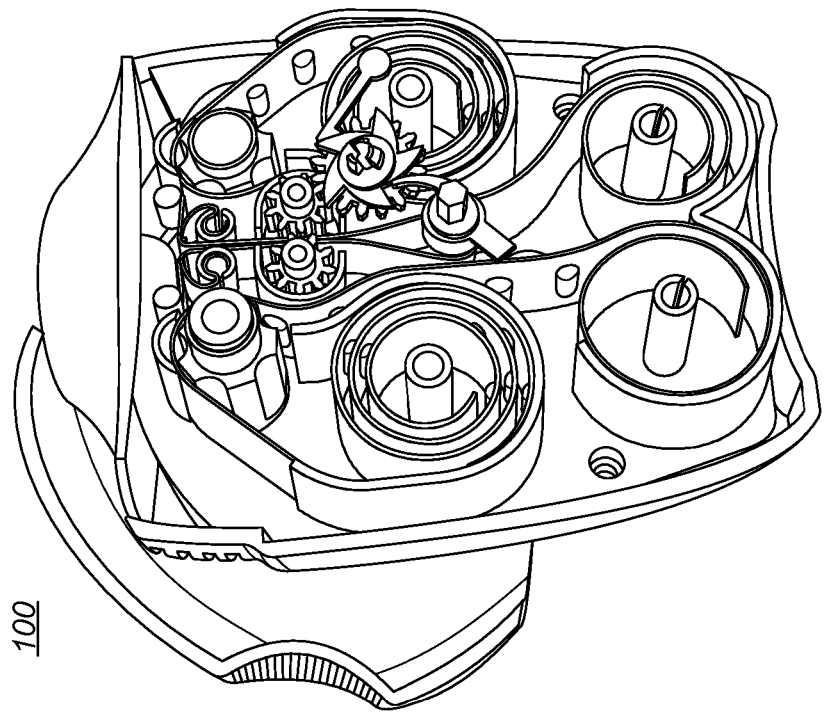
FIGS. 13A to 13D illustrate how an exemplary drive mechanism for the device might operate.
Figure 13A:
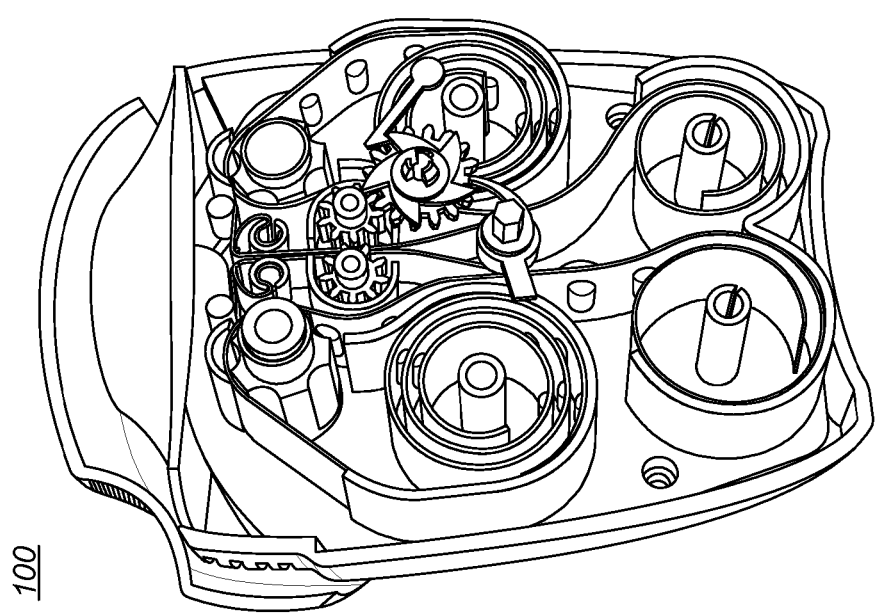

FIG. 13A illustrates the default position of the drive mechanism and backlash mechanism when the mouthpiece cover 104 is in the closed position. The latch arm 109 is engaged with the idler gear 158 preventing back-rotation of the idler gear 158.

To actuate the drive mechanism 101, the user pulls back on the mouthpiece cover 104 to the open position which exposes the mouthpiece of the device 100. This movement causes the mouthpiece cover 104 to rotate across an external face of the device 100. Since the mouthpiece cover 104 is connected to the driveshaft 162, rotation of the mouthpiece cover 104 causes rotation of the driveshaft 162. The drive arm 160, connected to the driveshaft 162, therefore also rotates at the same time as the mouthpiece cover 104 is opened, as shown in FIG. 13B. Rotation of the driveshaft 162 causes the drive arm 160 to engage with the idler gear 158, as shown in FIG. 13B, and cause rotation of the idler gear 158. As the idler gear 158 is being rotated in the allowed forward direction, the latch arm 109 disengages with the idler gear 158 allowing the idler gear 158 to freely move underneath the latch arm 109.

Figure 13D:
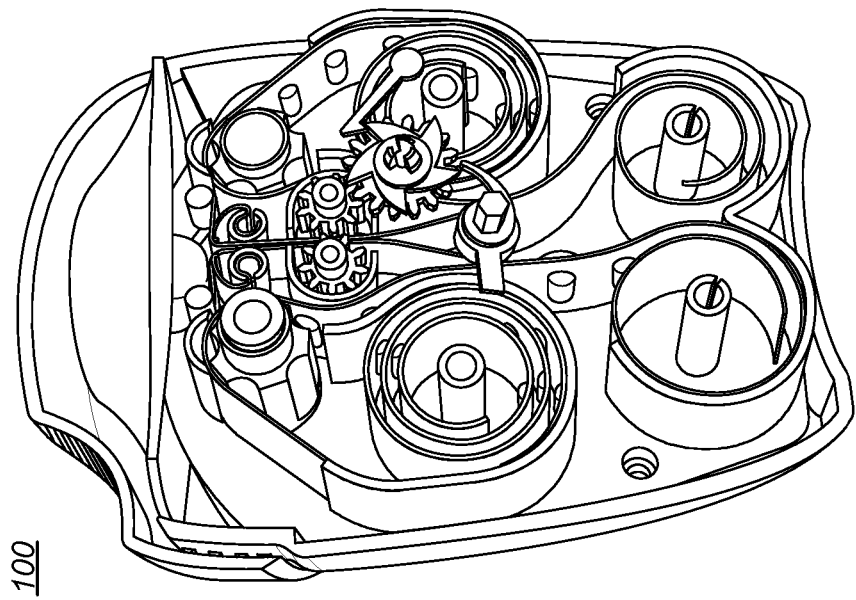
Figure 13C:
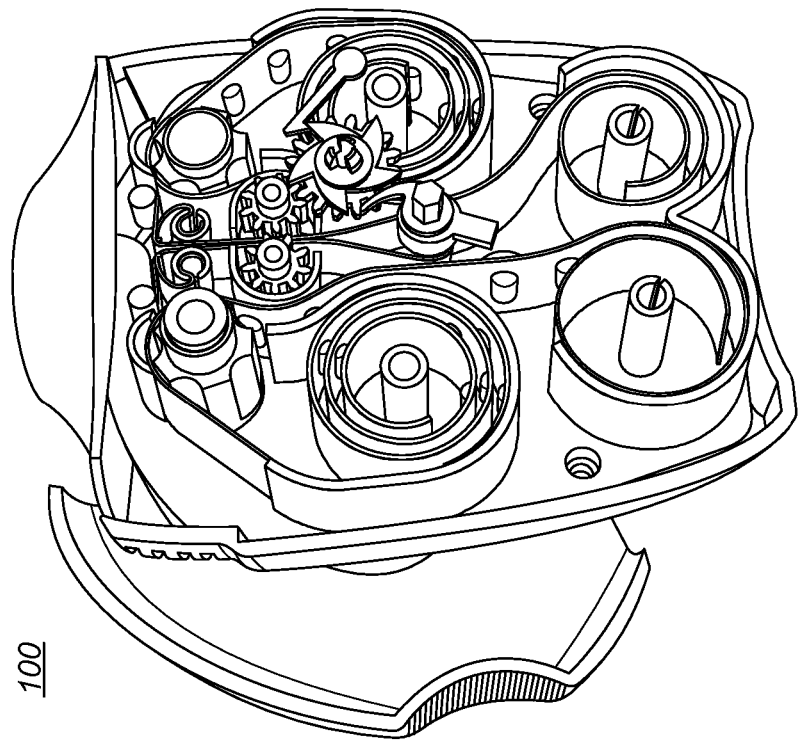

When the mouthpiece cover 104 has been opened fully, as shown in FIG. 13C, the drive arm 160 has been rotated to its maximum extent. As is clear from FIG. 13C, the drive arm 160 and the idler gear 158 rotate in opposite directions to each other. Here, the drive arm 160 rotates in an anticlockwise direction while the idler gear 158 rotates in a clockwise direction. Rotation of the idler gear 158 causes rotation of the first and second toothed wheels 127a, 127b which pull the sealing layer 122 through the opening mechanism 132. The mouthpiece cover 104 and drive arm 160 are configured to rotate by an amount that means that the two toothed wheels 127a, 127b pull the sealing layer 122 of the medicament carrier 116 through the opening mechanism 132 by an amount which is equal to the spacing between two adjacent compartments 118. Thus, one complete movement of the mouthpiece cover 104 from the closed to the open position causes the driving mechanism 101 to advance the medicament carrier 116 so that the next compartment is primed and the user can inhale the dose contained within the compartment 118.

After use, the mouthpiece cover 104 can be moved back to its closed position, as shown in FIG. 13D. During this movement, the driveshaft 162 is rotated in the opposite direction which causes rotation of the drive arm 160 in the reverse direction. As the drive arm 160 has a curvature which is opposite to the curvature of the teeth on the idler gear 158, the drive arm 160 simply rides over the teeth of the idler gear 158 back into its initial disengaged state. The latch arm 109 reengages with the idler gear 158 to prevent back-rotation of the idler gear 158 when the device 100 is not being used.

After the medicament carrier 116 has passed through the opening mechanism 132, the separated carrier strip 120 and sealing layer 122 are preferably retained together (and thereby stored) on a further "take-up" spool 129, as shown in FIG. 14A. They could alternatively be retained on separate spools, however. The separated carrier strip 120 and sealing layer 122 are wound together on a spool 129 to gather up any slack. In some embodiments (not shown), to save space and components, two medicament carriers 116 can be wound on the same take-up spool 129. A free end of the medicament carrier 116 is attached to the take-up spool 129 which retains and stores, by way of rotation, the separated medicament carriers 116 and sealing layer 122.

In order to ensure the sealing layer 122 is properly separated from the carrier strip 120 so as to open the compartments 118, the sealing layer 122 is placed under tension, of typically a few newtons of force. The tension in the sealing layer 122 is provided by a tensioning means 131. The particular choice of tensioning means 131 depends on the particular choice of geometry of the release member 134, for example the choice of blade geometry. As the release member 134 has a slot in its leading edge 134a, as shown in FIG. 5B, the driving mechanism 101 should include a tensioning mechanism 131.

Figure 14B:
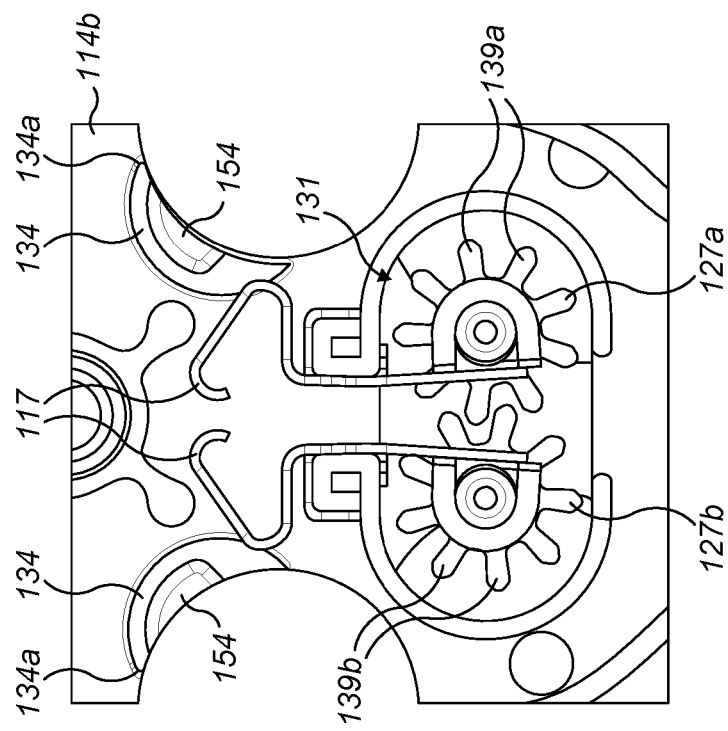
FIGS. 14A and 14B show a tensioning mechanism for the device.
Figure 14A:
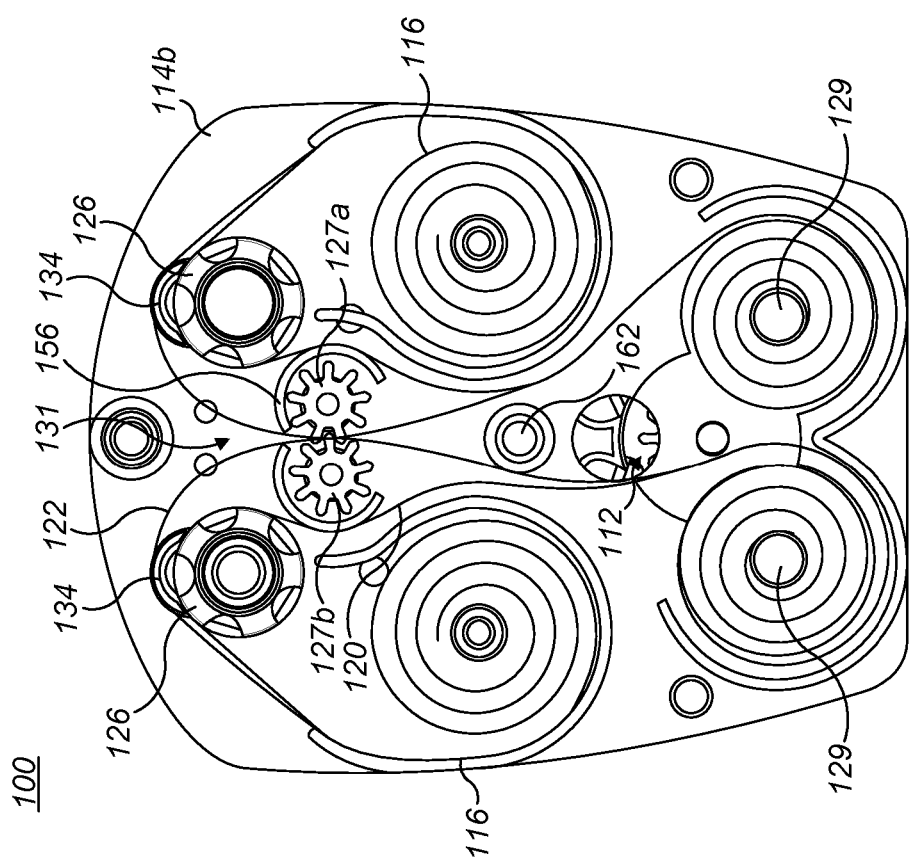

A tensioning mechanism 131, for applying controlled tension and positional control to the sealing layers 122 and medicament carriers 116, is illustrated in FIGS. 14A and 14B. This tensioning mechanism takes the form of a "mangle-type" tensioning mechanism 131. This tensioning mechanism 131 is provided by the components for the drive mechanism, in particular the pair of toothed drive wheels 127a, 127b.

Downstream of the release members 134, the separated sealing layer 122 of each medicament carrier 116 is fed between the two toothed drive wheels 127a, 127b. The respective teeth on the two drive wheels 127a, 127b interlock as they rotate, engaging the sealing layers 122 such that they are "mangled" between the rotating teeth, causing the sealing layers122 to deform as they are pulled through the tensioning mechanism 133. As the tensioning mechanism 131 draws the sealing layers 122 through it, tension is thereby applied to the separated portions of the sealing layers 122 upstream of the tensioning mechanism 131 (i.e. between the release members 134 and the tensioning mechanism 131).

The separated sealing layer 122 is fed around a sprung element 117, as better shown in FIG. 14B, to produce a controlled tension from a controlled displacement. The sprung element 117 is resiliently biased towards the outside of the device 100, as shown in FIG. 14B. Under tension, the sprung element 117 is forced towards the centre of the device 100. The sprung element 117 controls the tension by altering the path length along which the separated portion of sealing layer 122 travels by flexing either inwardly, towards the centre of the device 100, or outwardly, away from the centre of the device to its rest position. Specifically, if the tension in the separated portion of the sealing layer 122 is too high then the sprung element 117 rotates, or flexes, inwardly towards the centre of the device, which has the effect of shortening the path along which the sealing layer 122 travels and therefore accommodates the tension in the sealing layer 122 safely. If the tension in the sealing layer 122 is too low, the sealing layer 122 cannot hold the sprung element 117 in its flexed position, against the biasing force of the sprung element 117, and so the sprung element 117 returns to its rest position shown in FIG. 14B. This has the effect of extending the path along which the sealing layer 122 travels and so again accommodates the change in tension in the sealing layer 122. The sprung element 117 therefore regulates the tension in the separated portion of the sealing layer 122 by altering its path length.

The tensioning mechanism 131 thereby avoids the use of a clutch mechanism. A further advantage of the mangle tensioning mechanism 131 is that the desired tension in the sealing layer 122 can be maintained without the need to deal with a change in the diameter of a take-up spool 129 over time. This is because the effect of gripping the sealing layer 122 with the mangle-type mechanism 131, which matches or nearly-matches the index wheel speed, and therefore the speed of the carrier strip 120, is to pull the sealing layer 122 down against the sprung element 117, thereby providing a controlled tension.

In more detail, the mangle tensioning mechanism 131 comprises a plurality of mangle gears, each comprising a plurality of gripping teeth 139. In this embodiment of a device 100, the mangle gears are provided by the toothed drive wheels 127a, 127b. The gripping teeth 139, which generally do not have an involute profile, are equally spaced apart around the respective perimeters of the mangle gears 127. The mangle gears 127 are arranged next to each other such that the gripping teeth 139 of one mangle gear 127a engage with a space between the gripping teeth 139 of the other mangle gear 127b.

The cooperation of the gaps between the teeth 139a on one gear 127a with the gripping teeth 139b on the other gear 127b is important as it is this cooperation which allows the mangle gears 127 to grip the sealing layer 122 and draw the sealing layer 122 through the mangle-type mechanism 131.

After the sealing layer 122 has passed through the tensioning mechanism 131, tension in the sealing layer 122 is no longer required. This means that the sealing layer 122 and the empty medicament carrier 116 may simply be wound up on the take-up spool 129 which can be rotated at a constant speed.

The form of the gripping teeth 139 of the tensioning mechanism 131 is important for effective functioning of the tensioning mechanism 135. The form of the gripping teeth 139 is chosen to maximise the wrap angle of the sealing layer 122 whilst minimising the bending energy. In some embodiments, the teeth 139 have a 20 degree involute. It is important to ensure that the mangle gears 127 must not allow slippage. The bending energy required may be minimised by configuring the gears 127 to avoid sharp curves in favour of gentle curves along the path the sealing layer 122 follows through the gripping teeth 139.

As used herein, the term "wrap angle" may preferably connote the sum of the angles by which the sealing layer is wrapped around the teeth of the mangle gear 127. In other words, it may be considered to be the angle of contact of the sealing layer.

Ideally, the speed at which the mangle gears 127 are driven should speed-match the indexing wheel 126. In order to prevent the possibility of any slippage occurring, the mangle gears 127 can be very slightly over-driven. This can be achieved by using a compound gear and another gear wheel to increase the speed of the mangle gears 127 relative to the speed of the indexing wheel 126. In combination with a good long travel on the sprung element 117, this allows for a certain level of uncertainty in the amount of slip. As the tension forces on the sealing layer 122 increases, the feed rate through the mangle gears 127 drops to provide a negative feedback mechanism. To enable this, the mangle gears 127 are mounted on compliant axes, allowing the axes to be flexible and move slightly as the tension in the sealing layer 122 changes. The mangle gears 127 are therefore laterally sprung, meaning they can move both towards and away from each other. Thus, as well as controlling the speed at which the medicament carriers 116 are driven through the device, the mangle gears 127 form part of the negative feedback mechanism.

The mangle gears 127 are held between flexible spring-steel (not shown) so that the mangle gears 127 are held firmly in place and have a well-defined range of motion. It is the combination of the compliant axes and the flexible spring steel which provides the negative feedback mechanism. Advantageously, the negative feedback mechanism allows the speed of the mangle gears 127 to self-correct if the sealing layer 122 is excessively tight or under tension.

The take-up spools 129 can be driven at a constant rotation rate, which matches or is slightly less than the rotational speed that would result in the medicament carrier 116 and sealing layer 122 being wound up at the end of the life of the medicament device 100. In other words the take-up spools 129 are driven at the correct average rotational speed, which is averaged based on the total amount that the take-up spool will rotate for a complete medicament carrier 116 to be used in the device. As a result, the compartments 118 of the medicament carrier 116 are initially very loose, and incrementally tighten over time, noting that as more used medicament carrier 116 is stored on the take-up spool 129, the effective diameter of the combined take-up spool 129 and used medicament carrier 116 will change.

A guide member 156 is provided to surround, at least partially, each mangle gear 127a, 127b, which thereby guides the separated carrier strips 120 around the mangle gears 127.

Figure 15:
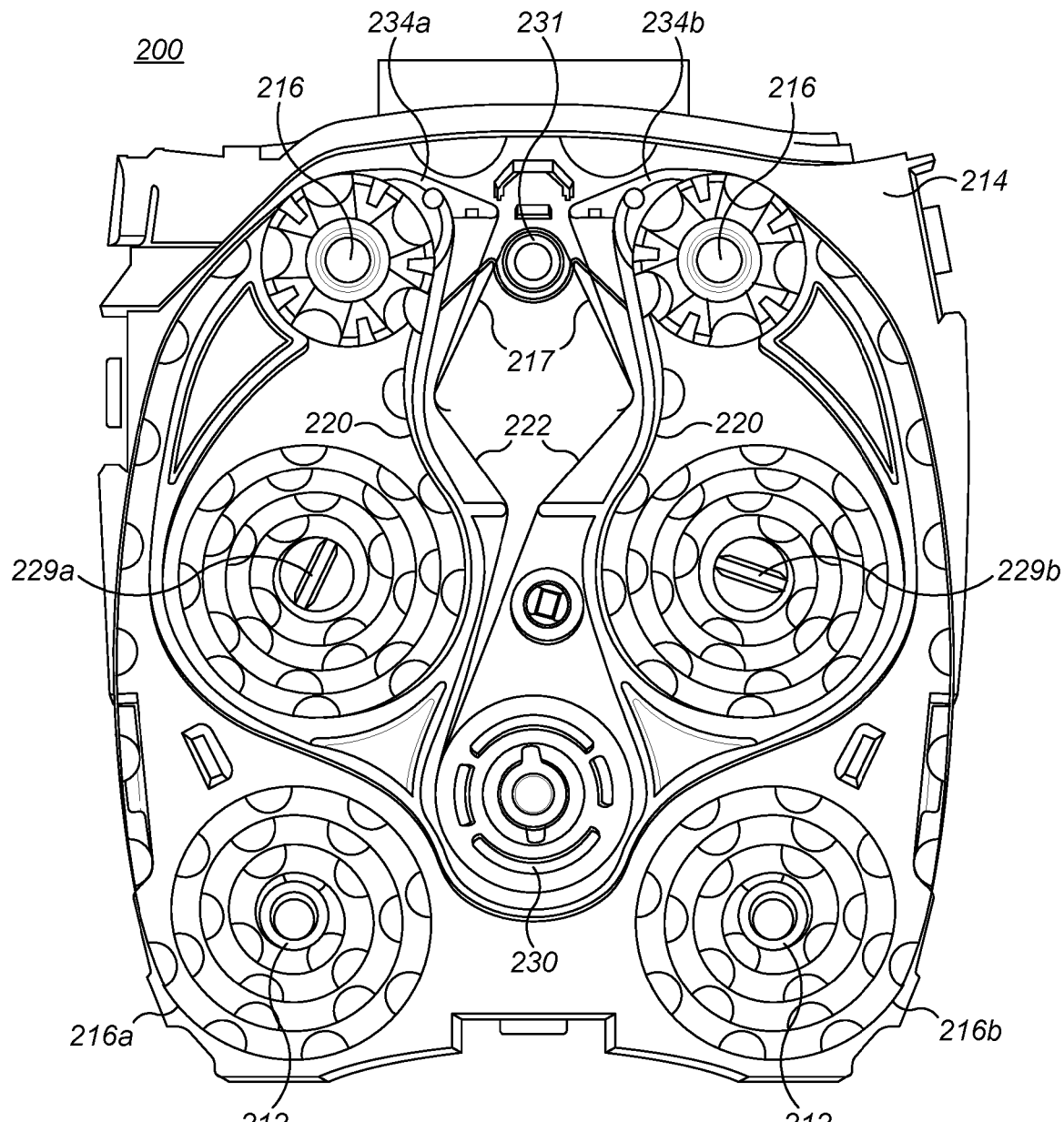
FIG. 15 show another embodiment of a medicament delivery device according to the present invention.

FIG. 15 shows another embodiment of a medicament device 200 according to the invention. Similar to the previously described embodiment, this device 200 comprises two medicament carriers 216a, 216b, initially stored on respective spools 212, and arranged to be fed by a pair of indexing wheels 226 through respective release members 234a, 234b. As before, the release members 234 are arranged to engage between the carrier strip 220 and sealing layer 222 so as to separate (e.g. to peel) the sealing layers 222 from the carrier strips 220.

In this embodiment, however, the two separated carrier strips 220 are stored separately on two take-up spools 229a, 229b, respectively, and the separated sealing layers 222 from the two medicament carriers 216a, 216b are stored together (i.e. wound) on a further take-up spool 230.

Ideally, a tensioning mechanism 231 is provided for applying controlled tension and positional control to the sealing layers 222 and carrier strip 220. In the embodiment shown, the tension mechanism 231 comprises resilient sprung elements 217 which control the tension by altering the path length along which the separated portions of sealing layer 222 travel by flexing either inwardly, towards the centre of the device 200, or outwardly, away from the centre of the device 200 to its rest position.

Figure 16A:
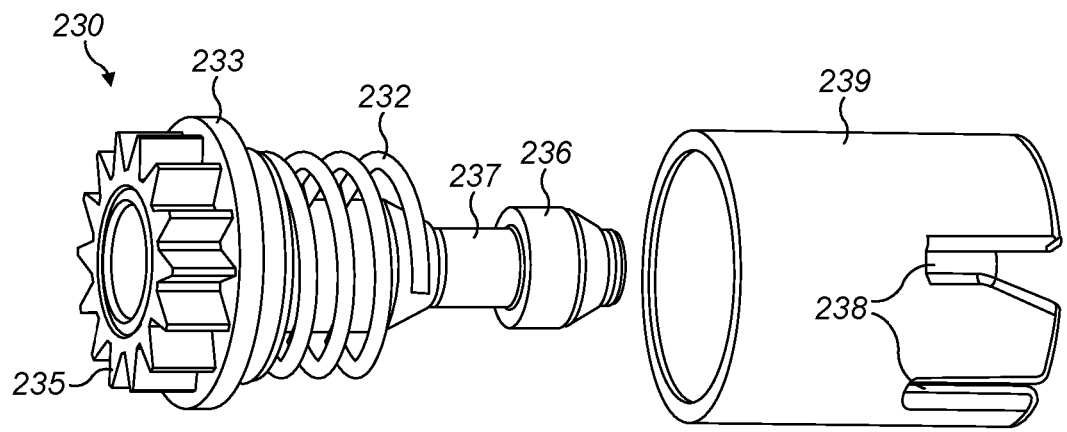
FIGS. 16A and 16B show the clutch mechanism of the take up spool in FIG. 15.
Figure 16B:
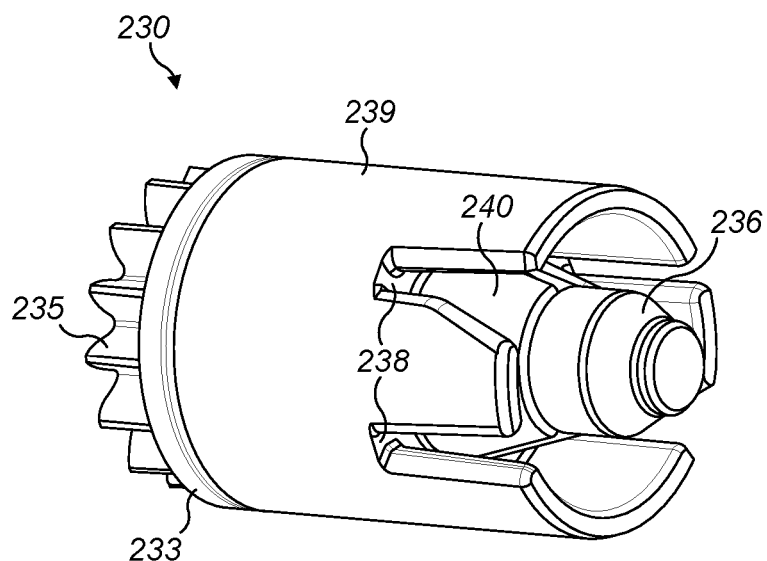

The take-up spool 230 for the sealing layers 222, positioned downstream of the tensioning mechanism 231, has a limited-slip clutch mechanism 228. The clutch mechanism 228 is preferably a friction clutch, as further illustrated in FIGS. 16A and 16B. As illustrated best in FIG. 16A, the clutch mechanism 228 comprises a shaft 237 attached at one end to a flanged base 233. A clutch spring 232 that extends partway along the shaft 237 is retained by the base 233. A gear wheel 235 provided on the other side of the flanged base 233 is arranged to be driven, in use, by movement of the mouthpiece cover. The take-up spool 230 includes a hub 239 having longitudinally arranged recesses or slots 238 for receiving therein free ends of the sealing layers 222, initially prior to use, so as to retain them when being wound up on the take-up spool 230. The hub 239 includes an internal portion 240 having a frustrated cone shape, through which the other end 236 of the shaft 237 passes. Said end 236 is bulbous-shaped (e.g. like a mushroom head), which inhibits its retraction back through the inner portion 240 of the hub 239.

The clutch spring 232 is sandwiched between the base 233 and the inner portion 240 of the hub 239, and as such provides a spring bias that urges the inner portion 240 of the hub 239 against the bulbous end 236 and creates frictional contact between the contacting surfaces such that they generally rotate together as a single unit.

As such, the hub 239 is usually rotated by the gear wheel 235. However, when the tension in one (or both) of the sealing layers 222 exceeds the friction between the inner portion 240 of the hub 239 and the end 236 of the shaft 237, the friction is overcome and the clutch mechanism 228 allows relative movement between the inner portion 240 and the shaft end 236, and thereby acts as a limited-slip clutch.

Figure 17B:
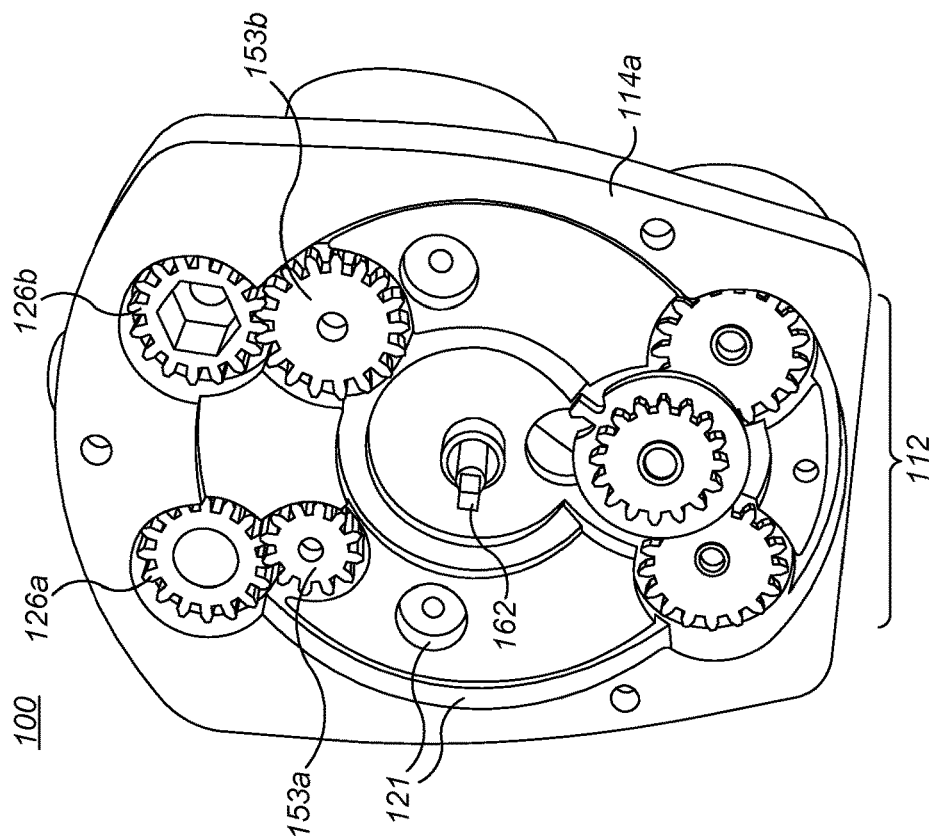
FIGS. 17A and 17B show a Geneva (counter) mechanism for the device of FIG. 1, with the tens ring and units ring mounted, and unmounted to show the gearing, respectively.
Figure 17A:
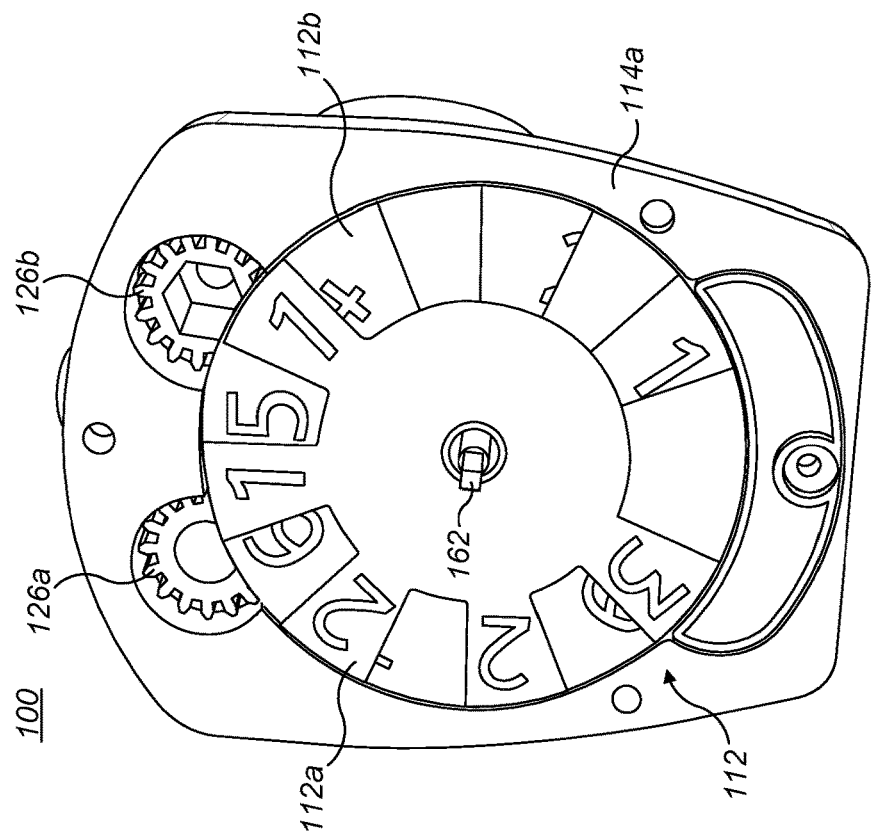

FIG. 17A shows the device 100 as shown in FIG. 12b, but now with a tens ring 112a and a units ring 112b of the counter mechanism 112 mounted to the device 100. FIG. 17B shows the Geneva mechanism behind the rings 112a, 112b, which drives the counter, via the driveshaft 162 mechanically linked to the mouthpiece cover 104.

By using a Geneva mechanism, the device counter 112 can be better integrated into the indexing (drive) mechanism, which further reduces the number of components in the device 100.

In addition to a "typical" Geneva mechanism, a "driven" Geneva mechanism may be used, where the Geneva wheel is the component which is driven, and can thus be an existing component of the device. The units ring may then be driven continuously off the Geneva wheel, and the intermittent ("tens") ring can be locked and driven off any of a variety of different types of Geneva features on a different layer of the Geneva wheel.

Furthermore, either a "typical" or a "driven" Geneva mechanism could be run using a fives ring rather than a tens ring. This may be advantageous if a component (e.g. the indexing wheel 126) rotates fully every five indexes, as it may then run on a one-to-one ratio with the units ring, thereby removing a layer of compound gears, and may double with the driven Geneva gear.

There are at least three options for the end of life counter behaviour. In each case, the intermittent ring covers the units ring; the first option involves the intermittent ring simply never indexing again by removing the drive surface in that region and retaining the lock surface; the second option involves retaining both the drive and the lock, causing the whole mechanism from the mouthpiece cover 104 onwards to lock down; the third option is as the second option, but with the component which fails when the user applies a large torque selected to achieve a particular outcome—for example, the input ratchet breaking so that the mouthpiece cover moves with no resistance (apart from retaining bumps), clearly communicating that the device is now broken and out of service.

Counter parts are noticeably easier to assemble and get the timing right for if the module of the gears is adjusted so that the number of teeth is a multiple of the number of stops which the units ring makes per rotation of the intermittent gear. The module of the gear teeth could therefore be set to make sure that that is the case.

While the foregoing is directed to an exemplary embodiment of the present invention, other and further embodiments of the invention will be apparent to those skilled in the art from consideration of the specification, and may be devised without departing from the basic scope thereof, which is determined by the claims that follow.

The invention claimed is:

1. A manifold for a medicament delivery device configured to deliver discrete doses of medicament contained in a plurality of individual compartments spaced along a carrier strip and sealed by a sealing layer to form a medicament carrier, the manifold comprising:
　　at least one opening mechanism comprising a release member arranged to engage between the carrier strip and the sealing layer of the medicament carrier so as to separate the sealing layer from the carrier strip and thereby open a compartment of the medicament carrier as it is advanced into an entrainment position,
　　wherein the release member includes a surface configured to cover the opened compartment when in the entrainment position so as substantially to contain the medicament dose of said opened compartment,
　　wherein the opening mechanism further comprises a cylindrical indexing wheel having a plurality of indentations spaced around its exterior surface, each indentation from the plurality of indentations configured to receive a compartment from the plurality of individual compartments of the medicament carrier therein such that rotation of the indexing wheel advances the medicament carrier and thereby moves the plurality of individual compartments of the medicament carrier sequentially into the entrainment position, and wherein the indexing wheel has an axial through-bore arranged to be in fluid communication with a side of said surface of the release member arranged to face the carrier strip such that the indexing wheel and the release member thereby form part of an entrainment airpath.

2. The manifold of claim 1, wherein the release member is further configured to provide an inlet and an outlet for air to pass through the opened compartment, when covered by the release member in the entrainment position, such that air can be directed through the opened compartment, via said surface of the release member, to entrain the medicament dose of said opened compartment, in said entrainment airpath.

3. The manifold of claim 2, further comprising a bypass airpath arranged to direct air to bypass the release member of the opening mechanism, wherein the entrainment airpath and the bypass airpath are arranged to merge downstream of the release member of the opening mechanism.

4. The manifold of claim 1, wherein the indexing wheel is positioned adjacent said surface of the release member such that the separated carrier strip passes between the indexing wheel and the release member.

5. The manifold of claim 4, wherein, while in the entrainment position, the opened compartment is retained within the indentation of the indexing wheel into which it is received, whereby subsequent rotation of the indexing wheel allows the compartment to be released from said indentation.

6. The manifold of claim 4, wherein said entrainment airpath is arranged to flow through the indexing wheel from a proximal end of the indexing wheel to a distal end of the indexing wheel, and then return along said surface of the release member from a distal end of the release member to a proximal end of the release member.

7. The manifold of claim 1, wherein the entrainment airpath is arranged to flow through the indexing wheel and then along said surface of the release member such that air flows in a first direction through the indexing wheel and then in a second direction along said surface of the release member, said first and second directions being generally opposed.

8. The manifold of claim 1, wherein said surface of the release member comprises at least one structural feature located on the side of said surface arranged to face the carrier strip, said structural feature being configured to disrupt the flow of air across said surface of the release member so to promote air flow through the opened compartment.

9. The manifold of claim 8, wherein the at least one structural feature is configured to disrupt any vorticity in the airflow.

10. The manifold of claim 1, wherein the release member comprises at least one curved surface arranged to bridge across a compartment when in the entrainment position.

11. The manifold of claim 1, wherein the release member has a leading edge configured to engage between the carrier strip and sealing layer, and a recess is formed in a portion of the leading edge of the release member.

12. The manifold of claim 11, wherein the recessed portion extends across a central portion of the leading edge.

* * * * *